US011724881B2

(12) United States Patent
Chila et al.

(10) Patent No.: US 11,724,881 B2
(45) Date of Patent: Aug. 15, 2023

(54) DISTRIBUTION AND INVENTORY SYSTEM AND METHODS OF USING THE SAME

(71) Applicant: Ethicon, Inc., Somerville, NJ (US)

(72) Inventors: Matthew Chila, Doylestown, PA (US); Jonathan Addeo Syby, Manasquan, NJ (US); Allen Keith On, Flemington, NJ (US); David Mickle Wade, Boca Raton, FL (US); Matteo Josue Piedra, Gladstone, NJ (US); Lewis Arthur Lau, Millington, NJ (US)

(73) Assignee: Ethicon, Inc., Rartian, NJ (US)

( * ) Notice: Subject to any disclaimer, the term of this patent is extended or adjusted under 35 U.S.C. 154(b) by 490 days.

(21) Appl. No.: 16/888,178

(22) Filed: May 29, 2020

(65) Prior Publication Data

US 2020/0377301 A1 Dec. 3, 2020

Related U.S. Application Data

(60) Provisional application No. 62/854,003, filed on May 29, 2019.

(51) Int. Cl.
 *B65G 1/137* (2006.01)
(52) U.S. Cl.
 CPC ................. *B65G 1/1375* (2013.01)
(58) Field of Classification Search
 CPC .................................................. B65G 1/1375
 See application file for complete search history.

(56) References Cited

U.S. PATENT DOCUMENTS

| 5,713,485 A | * | 2/1998 | Lift | G07F 17/0092 |
| | | | | 221/129 |
| 6,247,610 B1 | * | 6/2001 | Ziesel | G07F 9/02 |
| | | | | 221/121 |

(Continued)

FOREIGN PATENT DOCUMENTS

| CA | 2502489 C | 2/2014 |
| EP | 0 439 355 A2 | 7/1991 |

(Continued)

OTHER PUBLICATIONS

International Search Report and Written Opinion dated Sep. 24, 2020 received in International Application No. PCT/US2020/035239.

(Continued)

*Primary Examiner* — Kyle O Logan

(57) ABSTRACT

Systems, computer-readable instructions, and methods for dispensing and tracking medical products in various medical locations are disclosed. For example, the system may include a server which receives one or more requests for types of medical products from one or more client devices, determines whether the requested types and quantities are available in a dispenser and issues an instruction to the dispenser to automatically dispense the requested medical products and quantities. The server may receive confirmation after the types of medical products are dispensed from the dispenser and update a database. The server may receive unused and used medical product information from a client device and reconcile with restocked medical product information from the dispenser. Available types of medical products and quantities, usage reports and recommendations may be viewed via a Platform by one or more client devices. The dispenser may receive requests directly from a client device for medical products.

35 Claims, 16 Drawing Sheets
(2 of 16 Drawing Sheet(s) Filed in Color)

(56) References Cited

U.S. PATENT DOCUMENTS

| | | | |
|---|---|---|---|
| 7,228,200 B2 | 6/2007 | Baker et al. | |
| 7,748,628 B2* | 7/2010 | Greyshock | G07F 11/62 |
| | | | 235/462.01 |
| 2013/0118094 A1* | 5/2013 | Laspia | E04H 1/00 |
| | | | 52/79.1 |
| 2013/0231775 A1* | 9/2013 | Jefferies | G06Q 20/34 |
| | | | 700/237 |
| 2014/0277704 A1* | 9/2014 | Memar | B01F 33/8442 |
| | | | 700/233 |
| 2014/0379123 A1* | 12/2014 | Hirshbain | G07F 9/001 |
| | | | 700/243 |
| 2016/0220323 A1* | 8/2016 | Forrest | G16H 40/60 |
| 2018/0260779 A1* | 9/2018 | Singh | G06Q 30/0282 |
| 2021/0030625 A1* | 2/2021 | Houghton | A61J 7/0436 |
| 2021/0312751 A1 | 10/2021 | Xu et al. | |
| 2021/0374658 A1 | 12/2021 | Chila et al. | |

FOREIGN PATENT DOCUMENTS

| | | |
|---|---|---|
| WO | 97/14393 A1 | 4/1997 |
| WO | 2013/067501 A1 | 5/2013 |
| WO | 2016/040593 A1 | 3/2016 |
| WO | 2016/109726 A1 | 7/2016 |

OTHER PUBLICATIONS

International Search Report and Written Opinion of the International Searching Authority dated Sep. 2, 2020 received in International Application No. PCT/US2020/035262.

\* cited by examiner

Fig. 5A
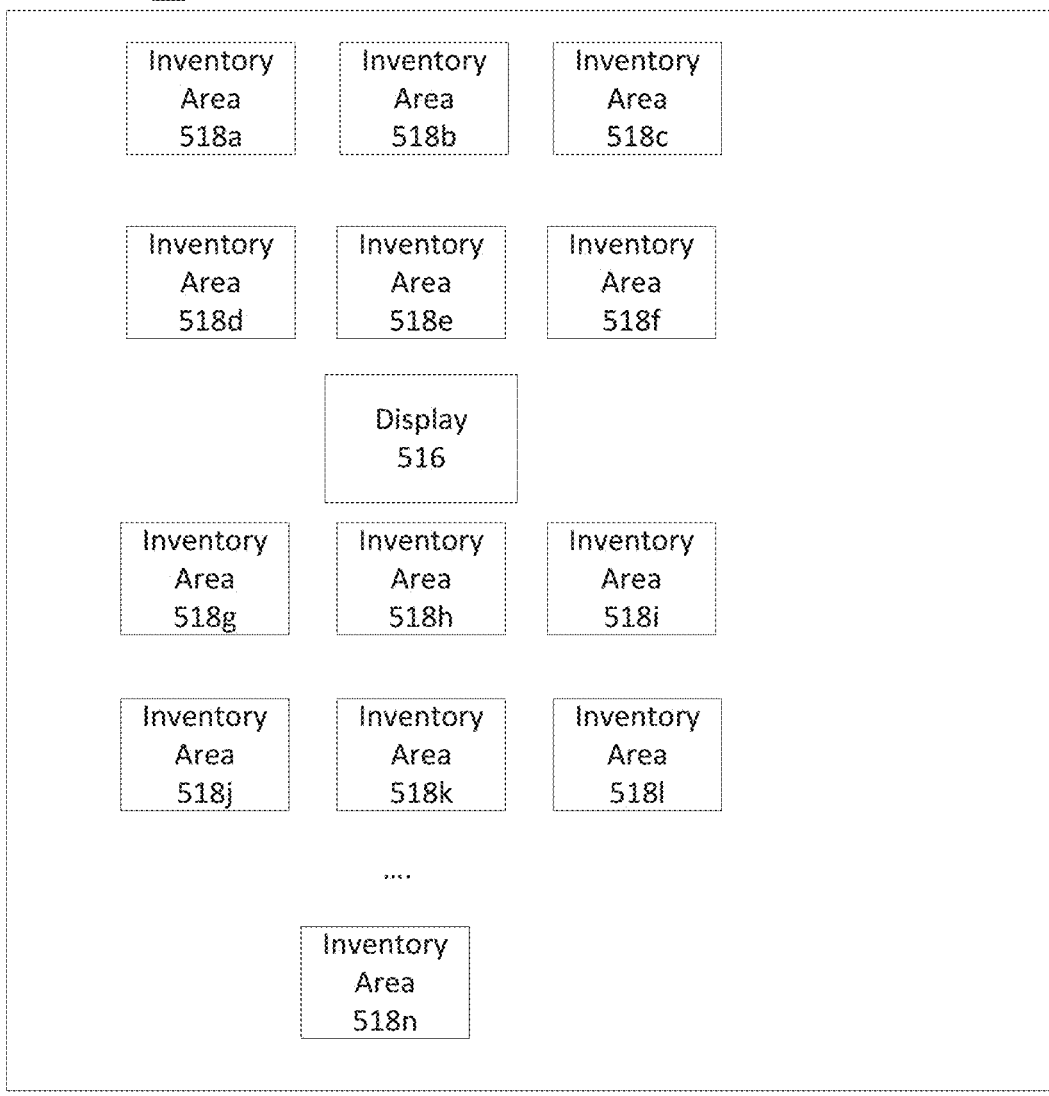
Fig. 5B

DISTRIBUTION AND INVENTORY SYSTEM AND METHODS OF USING THE SAME

CROSS-REFERENCE TO RELATED APPLICATION

This application claims the benefit of and priority to U.S. Provisional Application Ser. No. 62/854,003 filed May 29, 2019, the contents of which are incorporated herein by reference.

FIELD OF THE DISCLOSURE

The present disclosure relates to dispensing and inventorying of medical products, and more particularly to systems for dispensing and tracking inventory of medical products in various medical locations, such as hospitals, clinics, outpatient surgical centers, or any other location that dispenses various medical products for use during medical procedures.

BACKGROUND

In a typical hospital, many medical products are stored in a storage area, such as a closet or storage room. As one example, the storage and use of sutures is discussed. Typically, a hospital stores hundreds of different types of sutures on racks, in cabinets or in suture storage rooms. In this typical hospital, for any given surgical procedure, a surgeon will often have what is commonly referred to as a surgeon "preference card" that specifies what products (including the types of sutures) the surgeon expects to use for that procedure, and how many of each (quantity). These sutures and supplies are obtained by the circulating nurse or other hospital staff and made available and ready to use in the surgical theater. It is common practice for any such preference card to include more sutures of a given type than what is likely to be needed, and additional types of sutures than those likely to be used to account for uncertainties during the procedure, and to avoid having to send someone to physically retrieve additional products from the storage area during surgery should the need arise.

In current practice, surgeon preference cards are manually kept, and still often exist in physical card format as opposed to electronically. They are not updated regularly, and not updated each time a surgical procedure is performed to more accurately reflect what was actually used versus what was requested for that surgery. Thus, any errors and inefficiencies in supply are repeated over and over again for a given surgeon each time he/she performs surgery. Further, the hospital has no way of tracking these errors and inefficiencies at all, let alone relative to a particular surgeon. Preference card change management is not solely owned by the surgeon, nursing or materials management. Therefore, it leads to unsuccessful change management and remediation of surgeon preference cards. Service providers have built businesses on the remediation of surgeon preference cards, but their services are expensive and not done on a consistent basis. Procedural standardization of surgical products is a growing trend in healthcare to control costs.

After a surgery is complete, all non-used sutures are to be properly restocked in their respective original storage bins and/or boxes in the storage closet. In reality, however, non-used sutures are often simply placed in a general overflow box in a storage room or thrown away. The job of restocking from a general overflow box (or otherwise) is a very time intensive process. For each individual suture package that must be restocked, the responsible individual must match the identifying information on that package with the identification on the proper box in the storage room. As indicated previously, these storage rooms may contain up to hundreds of similarly sized and shaped suture boxes. The current process is so manually intensive and time consuming, that some larger hospitals have resorted to hiring full time employees just to restock and manage sutures.

This typical system leads to waste of sutures due to improper disposal or lack of restocking, and a higher incidence of product loss due to products passing their expiration dates. This typical system also does not track who is actually removing what type of suture or quantity of sutures from the storage closet, or if any unused sutures are actually ever restocked.

Further, storage of sutures within a typical hospital leads to waste. Because hospitals typically do not have a system to accurately and timely keep track of inventory, often either too many sutures are stored leading to waste due to expiration of those sutures, or too few sutures are stored leading to use of alternative sutures which may not be optimal for the specific procedure.

Also, restocking of inventory is a manual, time-consuming process, which typically includes a lag time of several days to account for shipping times, actual time for a person to manually restock, etc. Nurses and materials management staff usually split the responsibility of restocking surgical product. It is estimated that it takes hospital staff over 20 hours a week to manage and restock suture products in the hospital. In 2016, the Association of Perioperative Registered Nurses reported that the national average base compensation was $70,300. Therefore, it is estimated that it costs hospital employers over $35,000 to have their operating room nurses restock and manage their suture inventory.

Although the examples discussed above refer to sutures, any medical product can be included in as these typical examples.

Manual and automated dispensing machines are known and utilized for dispensing a wide variety of items ranging from snacks and hot meals to health-related items such as certain over-the-counter medications. The vast majority of these dispensing machines are vending machines that are utilized as point of sale devices. While dispensing and vending machines are utilized in many areas, they are not widely used in the health care market.

In the field of surgery, for example, surgeons and other medical professionals rely on access to rooms of inventory having boxes of inventory manually stocked by themselves and sales representatives of the medical product manufacturers. These rooms require manual inventory control and simply hold the medical product.

Typically, different stock keeping units, or SKUs, need to be segregated by attributes such as diameter of suture, length of suture, color of suture, suture material (non-absorbable and absorbable), needle type, etc. As one example, one surgical suture manufacturer, Ethicon, Inc. of Somerville, N.J., has thousands suture SKUs for various products. This could translate to thousands of different suture boxes on the shelves in a larger hospital supply room. Product identification on each of the boxes is relatively small, and must be read carefully to select the appropriate sutures listed on a surgeon preference card for a given procedure and must also be read carefully in order to restock unused sutures properly. Given the manual nature of the current process, there are significant efforts in selection and restocking and inventory tracking. As indicated previously, it is estimated that a typical medium sized hospital may lose tens of thousands of dollars per year due directly to inefficiencies in the system.

SUMMARY

Disclosed is a system comprising: an interface, a dispenser and a server. The interface may be accessible from a plurality of client devices. The interface may enable one or more requests for types of medical products and a quantity for each type to be sent to a server for an identified medical procedure. The dispenser may comprise a plurality of inventory areas, a plurality of dispensing bins, one or more readers, a first electronic storage device, a first communication interface and a first processor. The plurality of inventory areas may be for types of medical products. A type of medical product is storable in a respective area of the plurality of inventory areas. The plurality of dispensing bins may receive and store dispensed medical products for scheduled medical procedures, respectively. The one or more readers may be configured to read an identifier on medical products or a box of medical products. The server may comprise a second communication interface, a second electronic storage device and a second processor. The second electronic storage device may be configured to store a database.

The database may comprise information on scheduled medical procedures including requested types of medical products and quantity for each for the identified medical procedure and an identifier of a person who requested the types of medical products, an identifier of the respective scheduled medical procedure. The database may further comprise an inventory for each type of medical products, the inventory including, for each type of medical product in the dispenser, the identifier of the medical product, an available quantity of the medical product and an expiration date.

The second processor may be configured to receive the one or more requests from one or more client devices, update the database based on the one or more requests; and when a schedule for one or more scheduled medical procedures for a period of time is confirmed, the second processor may be configured to cause the second communication interface to transmit to the dispenser the schedule having one or more pick lists for each of the one or more scheduled medical procedures for the period of time. The one or more pick lists for each of the one or more scheduled medical procedures for the period of time includes the identifier of the scheduled medical procedure and an identifier of each type of medical product and quantity of each to be dispensed. The schedule indicates a time of each of the one or more scheduled medical procedures.

In response to receipt of the schedule with the one or more pick lists for each of the one or more scheduled medical procedures for the period of time, the first processor may be configured to determine whether at least one of the plurality of dispensing bins for storing dispensed medical products is available and located in one of a plurality of dispensing areas, and in response to determining that at least one of the plurality of dispensing bins is available and located in one of the plurality of dispensing areas, the first processor is configured to cause, for an available bin, an automatic dispensing of the medical products for a pick list of the one or more pick lists for each of the one or more scheduled medical procedures included in the received schedule. The automatic dispensing may comprise retrieving the medical products from the corresponding inventory areas and placing the medical products in the one of the plurality of dispensing bins in the dispensing area for the pick list.

In an aspect of the disclosure, the schedule with the one or more pick lists for each of the one or more scheduled medical procedures for the period of time may further include location identifiers indicating a location of the inventory areas of the types of medical products, respectively from among the plurality of inventory areas, to be dispensed for each of the one or more pick lists for each of the one or more scheduled medical procedures. In this aspect, the first processor may cause the retrieval of the medical products using the location identifiers indicating the location.

In an aspect of the disclosure, in response to determining that at least one of the plurality of dispensing bins is not available, the first processor may repeat the determination.

In an aspect of the disclosure, when the dispensing based on the received schedule is complete or when the dispensing of one pick list is complete, the first processor may cause the dispenser to transmit, via the first communication interface, a confirmation to the server. In this aspect, the confirmation may include the types of medical products and quantities dispensed for each pick list that is completed. In response to receipt of the confirmation, the second processor may update the database.

In an aspect of the disclosure, the one of the one or more readers may scan one or more boxes of medical products for replenishing medical products. In this aspect, the first processor may transmit, via the first communication interface, a confirmation after changing a mode of operation, the confirmation including one or more identifiers of the one or more boxes. In response to receipt of the confirmation, the second processor may update the database.

In an aspect of the disclosure, the dispenser may further comprise a restocking area configured to store medical products which were previously dispensed and unused in a scheduled procedure. In this aspect, the first processor may cause the dispenser to determine whether the restocking area contains medical products for restocking and in response to the determination, the first processor may cause the dispenser to restock the medical products from the restocking area when the type of medical product is a type of medical product stored in the dispenser.

In an aspect of the disclosure, the restocking may comprise for each medical product, scanning the identifier of the medical product with an internal reader, determining the corresponding inventory area of the plurality of inventory areas for the type, and placing the medical product in the corresponding inventory area.

In an aspect of the disclosure, upon completion of restocking or periodically, the first processor may cause the dispenser to transmit, via the first communication interface, a confirmation to the server for reconciliation. The confirmation may include the type of medical product and quantity of each type.

In an aspect of the disclosure, the dispensing medical products to the plurality of dispensing bins may have priority over restocking. In this aspect, in response to receipt of a new schedule having one or more pick lists for a scheduled medical procedure and determining that one of the plurality of dispensing bins is available and located in one of the plurality of dispensing area or a pick list contained in a previous schedule had not been completed and determining that one of the plurality of dispensing bins is available and located in one of the plurality of dispensing area, the first processor may cause the dispenser to interrupt the restocking. The interrupt may be after a completion of restocking any scanned medical products at the time of receipt of the new schedule or determination.

In an aspect of the disclosure, the server may receive the quantity of used and unused medical products in a medical procedure from a client device, for each type of medical device in the one or more pick lists for the medical procedure. In this aspect, the second processor may compare the quantity of unused medical products for each type of medical devices, with the quantity of restocked medical products for each type of medical devices received from the dispenser for reconciliation.

In an aspect of the disclosure, in response to a discrepancy in the quantity of unused medical products and the quantity of restocked medical products, the second processor may cause the server to transmit, via the second communication interface, a notification to materials management or update a screen on a web-based user portal.

In an aspect of the disclosure, dispenser may further comprise an error bin. In this aspect, the dispenser when dispensing medical products may scan a medical product using an internal reader, and upon determining a medical product has expired, the first processor may cause the dispenser to place the expired medical product in the error bin.

In an aspect of the disclosure, the received schedule may also include, for at least one type of medical product, an allowable substitute medical product. In this aspect, in response to an error in attempting to dispense the at least one type of medical product, the first processor may cause the dispenser to dispense the allowable substitute medical product for the scheduled medical procedure in the schedule with the pick list and place the allowable substitute medical product in the appropriate dispensing bin.

In an aspect of the disclosure, the error may comprise attempting to retrieve the at least one type of medical product a set quantity of times.

In an aspect of the disclosure, the dispenser may further comprise a light indicator. In this aspect, when the allowable substitute medical product is dispensed in the dispensing bin, the light indicator may emit a set color different than when the dispensing bin in the dispensing area does not include the allowable substitute medical product.

In an aspect of the disclosure, when the allowable substitute medical product is dispensed, the dispenser may transmit to the server a confirmation indicating the type of medical products dispensed and the quantity, the type including the allowable substitute medical product.

In an aspect of the disclosure, the system may further comprise a second type of dispenser containing a plurality of types of medical products. The second type of dispenser may have a third communication interface which is configured to communicate with the server.

In an aspect of the disclosure, when a medical product is removed from the second type of dispenser, the second type of dispenser may identify the type of medical product and transmit the type of medical product that was removed to the server. In this aspect, the second processor may update the database based on the received type of medical products from the second type of dispenser. In an aspect of the disclosure, the second type of dispenser may have the same types of medical products as the first type of dispenser.

In an aspect of the disclosure, the second processor may generate a message when a quantity of available medical product for a type is less than a threshold, The quantity of available medical product may be determined based on the updated database including information from the dispenser.

In an aspect of the disclosure, the second processor may analyze, for each type of medical product, the used and unused medical products, for the same medical procedure over a time, using the information in the database and generate a report containing the analysis. The analysis may include a recommended type and quantity for each recommended type for each of the medical procedures. In an aspect of the disclosure, the second processor may analyze, for each type of medical product, the used and unused medical products, for the same provider over a time, using the information in the database and generate a report containing the analysis. The analysis may include a recommended type and quantity for each recommended type of medical product.

In an aspect of the disclosure, the reports may be accessible via Internet.

In an aspect of the disclosure, the second processor may analyze for each type of medical product, the used and unused medical products, for medical procedures over a time, and based on the analysis may issue a recommendation for ordering new medical products.

In an aspect of the disclosure, the medical products may be sutures, clips, fasteners, implants, hemostats (absorbable), orthopedic pins, screws, rods, plates, staple reloads, dressings, pacing wires, an endoscope, a clamp, a saw, bone wax, drains, connectors, adapters, tubing, or topical skin adhesives.

In an aspect of the disclosure, the plurality of inventory areas may be storage cartridges.

In an aspect of the disclosure, the interface may be accessible via Internet.

In an aspect of the disclosure, the server may transmit via the second communication interface, inventory data from the database to one or more client devices for display on a screen. In this aspect, the inventory data may be transmitted based on access rights for users of the one or more client devices.

In an aspect of the disclosure, all pick lists of the one or more pick lists for the same medical procedure are dispensed in the same available dispensing area.

In an aspect of the disclosure, the first processor, for each available bin, may cause an automatic dispensing of the medical products for a respective pick list of the one or more pick lists for each of the one or more scheduled medical procedures included in the received schedule. The automatic dispensing may comprise retrieving the medical products from the corresponding inventory areas and placing the medical products in a respective one of the plurality of dispensing bins in a respective one of the plurality of dispensing areas.

In an aspect of the disclosure, the system may further comprise a third processor configured to determine the types of medical products to be stored in the plurality of inventory areas; and for the determined type, determine a quantity of the plurality of inventory areas assigned. In an aspect of the disclosure, the determinations are sent to the second processor.

In an aspect of the disclosure, the determinations may be based on historical medical product use information received from a hospital where the dispenser is to be deployed for a plurality of medical procedures for a period of time. In an aspect of the disclosure, the third processor is configured to output a first coverage based on the determinations.

In an aspect of the disclosure, a coverage may be periodically determined based on the updated database. When the determined coverage is a threshold less than the first coverage, the third processor may execute the determination of the types of medical products to be stored in the plurality of inventory areas; and for the determined type, and the determination of the quantity of the plurality of inventory areas assigned again.

Also disclosed is a system comprising an interface and a dispenser. The interface may be accessible from a plurality of client devices. The interface may be for enabling one or more requests for types of medical products and a quantity for each type to be sent to a dispenser for an identified medical procedure. The dispenser may comprise a plurality of inventory areas, a plurality of dispensing bins, one or more readers, a first electronic storage device, a first communication interface and a first processor. The plurality of inventory areas may be for types of medical products. A type of medical product is storable in a respective area of the plurality of inventory areas. The plurality of dispensing bins may receive and store dispensed medical products for scheduled medical procedures, respectively. The one or more readers may be configured to read an identifier on medical products or a box of medical products. The first processor may be configured to receive the one or more requests for types of medical products and the quantities for each type via the first communication interface; and cause the dispenser to automatically dispense the requested types of medical products and the requested quantities for each type when available, to a dispensing bin, when the dispensing bin is available and in a dispensing area.

In an aspect of the disclosure, the system may further comprise a server. The server may comprise, a second communication interface; a storage device configured to store a database and a second processor. After the dispenser automatically dispenses the requested types of medical products and the requested quantities for each type, the second processor may receive confirmation from the dispenser via the second communication interface and update the database based on the confirmation.

BRIEF DESCRIPTION OF THE DRAWINGS

The present disclosure will be better understood by reference to the following drawings, which are provided as illustrative of certain embodiments of the subject application, and not meant to limit the scope of the present disclosure. The patent or application file contains at least one drawing executed in color. Copies of this patent or patent application publication with color drawing(s) will be provided by the Office upon request and payment of the necessary fee.

FIG. 5A-5C illustrates an example of a second type of dispenser in accordance with aspects of the disclosure;

DETAILED DESCRIPTION

As used herein, the term "medical product" refers to products such as sutures, clips, fasteners, implants, hemostats (absorbable), orthopedic pins, screws, rods, plates, staple reloads, dressings, pacing wires, an endoscope, a clamp, a saw, bone wax, drains, connectors, adapters, tubing, topical skin adhesives, etc. that can be stored in a dispenser. The dispenser is further described below, but can refer to any device that is configured to store one or more medical products, dispense and/or allow access to that medical product, maintain and/or provide an inventory of stored products.

Figure 1:
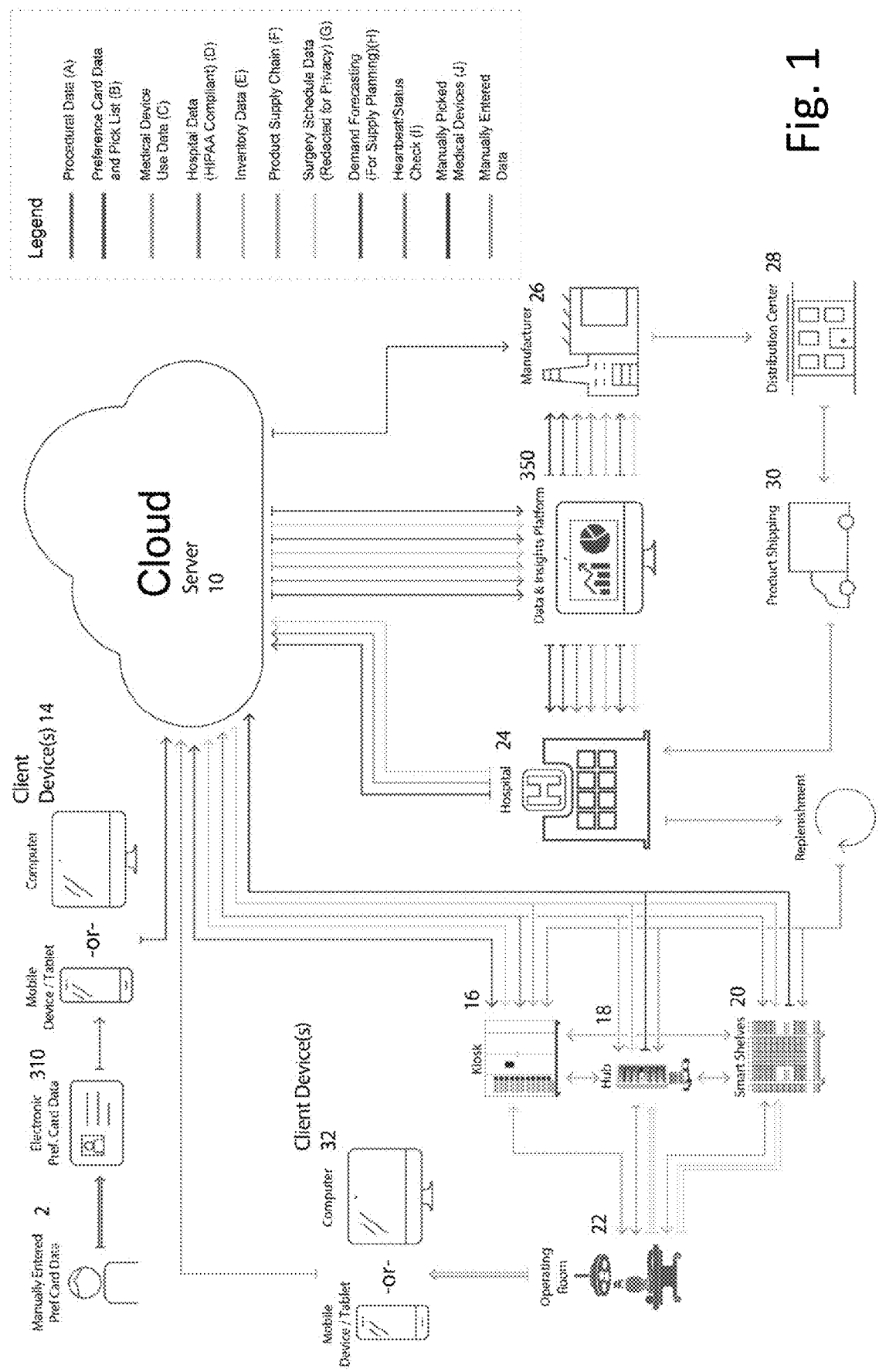
FIG. 1 is an illustration of an overview of a system in accordance with aspects of the disclosure.

The dispenser may be a first type of dispenser or a second type of dispenser. The first type of dispenser can dispense medical products via automation and receive unused medical products back into a storage compartment of the dispenser for automated restocking. An example of the first type of dispenser is shown in FIG. 1 as "Kiosk" 16. The second type of dispenser can dispense medical products via manual removal of a medical product. Examples of the second type of dispenser are shown in FIG. 1 as "Smart Shelf" 20 and "Hub" 18.

In the discussion and claims herein, the term "about" indicates that the value listed may be somewhat altered, as long as the alteration does not result in nonconformance of the process or device. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would either completely flat, or so nearly flat that the effect would be the same as if it were completely flat.

As used herein terms such as "a", "an" and "the" are not intended to refer to only a singular entity, but include the general class of which a specific example may be used for illustration.

As used herein, terms defined in the singular are intended to include those terms defined in the plural and vice versa.

The system is discussed below in reference to FIG. 1. Representative information flow is shown by various color lines between elements of FIG. 1. Although FIG. 1 includes a legend of what the colored lines refer to, they are further described below.

The system comprises a server 10. The server 10 is identified in FIG. 1 as "Cloud Server". The server 10 manages the inventory of medical products. Additionally, the server 10 generates and transmits a pick list from electronic preference cards 310 received from client devices 14 and causes a first type of dispenser to dispense the medical products. The server 10 may be managed by a manufacturer of the medical products. In other aspects of the disclosure, the server 10 may be managed by a third party (a party other than the hospital or manufacturer). The server 10 may be accessed by different client devices (terminals) 14, 32.

For example, one type of client devices 14 may be client devices having stored the electrical preference cards 310. These client devices 14 may be a mobile telephone, tablet, portable laptop, personnel computer or any electronic device with a memory and a communication interface. The communication interface may be a wireless communication interface. In other aspects of the disclosure, the communication interface may be a wired communication interface. In some aspects of the disclosure, the client device 14 may have a web browser and access the server 10 via the Internet. In other aspects of the disclosure, the client device 14 may have or download an application program and the application program is configured to access the server 10. In other aspects of the disclosure, the client device 14 may communicate with the server 10 using a file transfer protocol (FTP). In other aspects of the disclosure, the client device 14 may communicate with the server 10 using another secure data transfer method.

In accordance with aspects of the disclosure, the client device 14 transmits electronic preference card data 310 to the server 10. This communication may be bi-directional. For example, the server 10 may confirm receipt of the electronic preference card data 310.

The client device 14 can be located in a hospital 24, surgery center, in the surgeon's office, can be carried by the surgeon or healthcare provider, or can be in any other suitable location that has the ability to transmit the data of the electronic preference card 310 to the server 10.

Figure 2:
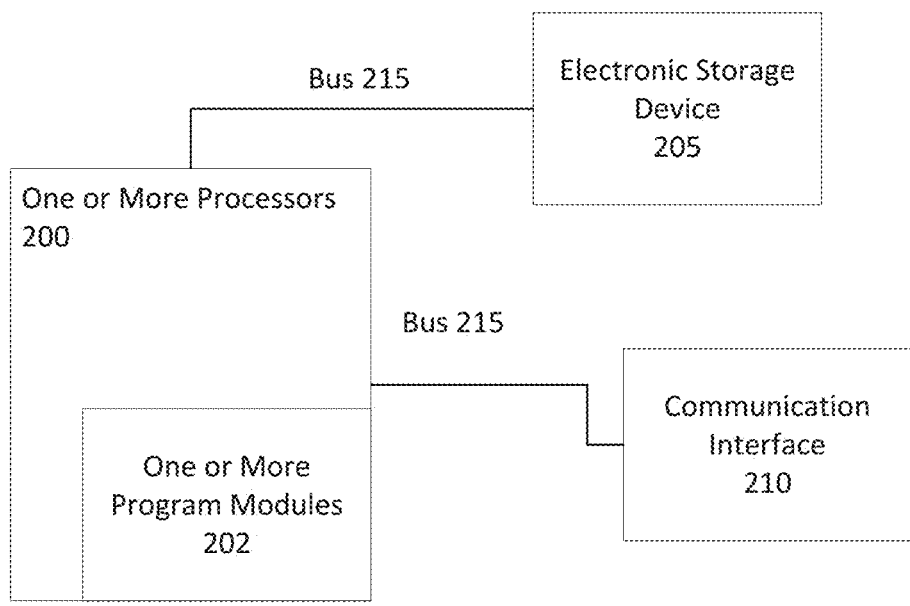
FIG. 2 is a block diagram of a server in accordance with aspects of the disclosure.

FIG. 2 illustrates a block diagram of the server 10. The server 100 comprises one or more processors 200, an electronic storage device 205, a communication interface 210 and a bus 215. The one or more processors 200 may be CPUs. The processor may be a single core or multiple core processor. In other aspects, some of the processors 200 may be GPUs. In other aspects, the processors 200 may be integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. When multiple processors 200 are used, the different processors may be of a different type. For example, one processor may be a CPU and another processor may be a GPU or an ASIC.

Electronic storage device 205 can include computer system readable media in the form of volatile memory, such as random access memory (RAM) and/or cache memory or others. In some aspects, multiple electronic storage devices 205 may be used. The electronic storage device 205 may be any type of integrated circuit or other storage device adapted for storing data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

The processors 200 may include program module(s) 202 that performs the methods and functions described herein. The module(s) 202 may be programmed into the integrated circuits of the one or more processors 200, or loaded from the electronic storage device 205. The bus 215 couples various system components including electronic storage device 205 to the one or more processors 200.

In some aspects, different processors may execute different functions described herein. For example, one processor may execute the inventory management in the first type of dispensers and the second type of dispensers and generate a pick list and another processor may execute configuration management for the first type of dispensers and the second type of dispensers, such as generating a planogram for each dispensers and publishing the same. For purposes of this description herein, description will use "a processor 200 in the server 10".

A planogram is a map of rows and columns within the dispensers (first type of dispensers and second type of dispensers). As will be described later, the generating of the planogram includes determining which types of medical devices will be included in a particular dispenser and number of slots or inventory areas. In some aspects, the size of the inventory areas may be different.

In some aspects, when multiple processors are used, the processors 200 may be connected to each other via a network.

In an aspect of the disclosure, the server 10 may have an architecture using micro-server layers include one or more micro-services for different functions and a API manager. The API manager contains the application programming interfaces (API) for the micro-services. The server 10 may also include an IoT hub and a data orchestration connected thereto to receive messages from client devices and direct the same to the appropriate micro-service layer.

The communication interface 210 may be a wireless communication interface. In other aspects, the communication interface 210 may be a wired communication interface.

Figure 3:
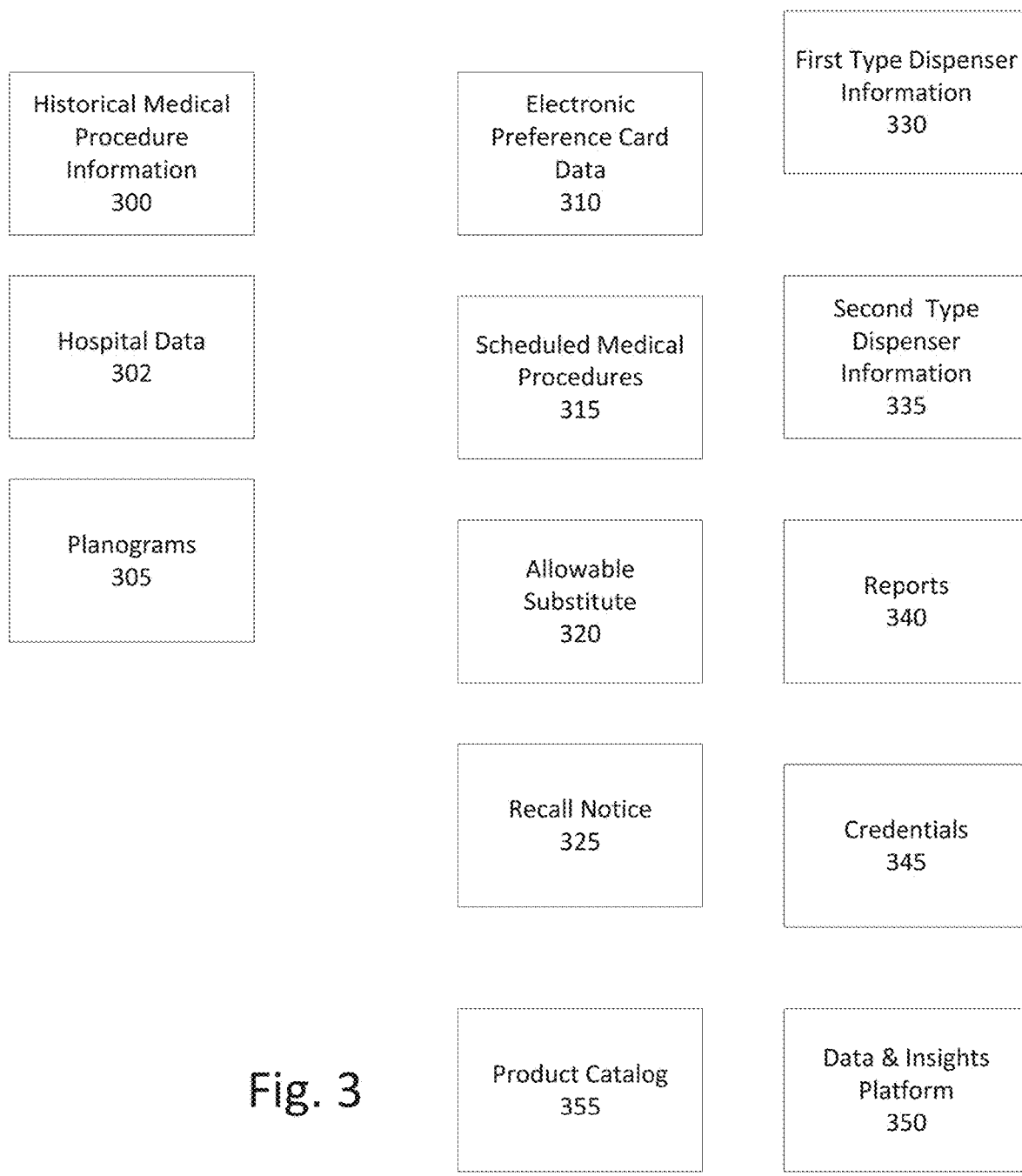
FIG. 3 is a block diagram of an electronic storage device in accordance with aspects of the disclosure.

FIG. 3 illustrates a block diagram of the electronic storage device 205 in accordance with aspects of the disclosure. The electronic storage device 205 includes historical medical procedure information 300. This information 300 is used by a processor 200 in the server 10 to generate the planogram for each dispenser. The historical medical procedure information 300 is obtained for a period of time prior to deployment of the system. For example, the period of time may be 4 months of information. In other aspects, the period of time may be longer. Historical medical procedure information 300 is obtained from a target location such as a hospital, clinics, out-patient surgical centers, or any other location that dispenses various medical products for use during medical procedures.

The historical medical procedure information 300 may include an identifier of a medical procedure, date and time, an identifiers of medical devices used, and quantities of each. In some aspects, the historical medical procedure information may also include the provider name(s). The provider name is the surgeon whom performed the medical procedure. In some aspects, the historical medical procedure information 300 may include a location of the operating room and identifier of a core. A core is a group of operating rooms in a specific area. In an aspect of the disclosure, the historical medical procedure information 300 may include a description of the medical procedure.

The electronic storage device 205 may also include hospital information 302. This information from the hospital 302 may also include various hospital data, including but not limited to name of the hospital, location of the hospital, number of operating rooms in the hospital, names and number of surgeons associated with the hospital, storage space at the hospital, and number and type of dispensers (such as dispenser 16, 18, 20) at the hospital, names of hospital personnel and job title. All of the hospital data can be appropriately redacted and transmitted according to the appropriate Health Insurance Portability and Accountability Act (HIPAA) standards. Hospital 24 used herein also includes clinics, out-patient surgical centers, or any other location that dispenses various medical products for use during medical procedures.

The electronic storage device 205 also includes the determined planograms 305 for each dispenser 16, 18, 20. The electronic storage device 205 also includes data from the electronic preference card 310 received from the client devices (electronic preference card data 310). The data 310 includes all of the preference card data from a plurality of client devices.

The electronic storage device 205 also includes scheduled medical procedures 315. This may be a list of the medical procedures. A scheduled medical procedure is a medical procedure having instructions originating from any client device and sent to the server with a specific time.

The information for the scheduled medical procedure 315 may include an identifier of the medical procedure, a date and time of the medical procedure and an identifier of the provider(s). In some aspects, the information may also include the operating room number and core identifier. In some aspects, the hospital 24 may send the information of a scheduled medical procedure. In other aspects, the server 10 may poll client devices for the scheduled medical procedure information. The schedule data can be appropriately redacted so the identity of the patient is not recorded or transmitted. In an aspect of the disclosure, the information for the scheduled medical procedure 315 may include some description of the medical procedures (e.g. procedural data). In other aspects, the procedural data may be separately transmitted.

The electronic storage device 205 may also include allowable substitute information 320. The allowable substitute information includes identifiers of medical products that may be used instead of a requested medical product from the electronic preference card data 310. The allowable substitute information is decided in advance by a provider or a hospital administrator. In other aspects of the disclosure, the allowable substitute information 320 may be received from the manufacturer 26.

The electronic storage device 205 may also include recall notices 325. The recall notices may be received from the manufacturer 26. The recall notices 325 include the identifier of the medical product recalled.

The electronic storage device 205 may also include first type dispenser information 330 for each first type of dispenser (e.g., Kiosk 16). The information 330 is separately kept for each first type dispenser 1-N. Each first type dispenser information 330 includes the identifier of the dispenser, the generated planogram for the dispenser, inventory information for each inventory area, e.g., identifier of the medical device associated with the inventory area and quantity. The first type dispenser information 330 may also include the pick lists generated for the dispenser, received picked medical device from the dispenser, unused medical devices received from a client terminal 32 and restocked medical devices received from the dispenser. The first type dispenser information 330 may also include status information from the dispenser such as error messages and confirmations.

The electronic storage device 205 also includes second type dispenser information 335 for each second type of dispenser (e.g., Hub 18 and Smart Shelf 20). The information 335 is separately kept for each second type dispenser 1-N. Each second type dispenser information 335 includes the identifier of the second type of dispenser, the generated planogram for the second type of dispenser, inventory information for each inventory area, e.g., identifier of the medical device associated with the inventory area and quantity.

The items may be stored in a form of a database. In some aspects, the items may be stored in one database. In other aspects, the items may be stored in separate databases which may be connected.

The electronic storage device 205 may also include reports 340. The reports 340 may be generated by the server 10 as described later. The reports 340 may be periodically generated such as daily, weekly, monthly, quarterly, etc. For example, the reports 340 may be generated by analyzing the inventory in the first type dispenser information 330 and/or the inventory in the second type dispenser information 335 separate from or in combination with the electronic preference card data 310 or usage information. The reports 340 may include the underlying data used to generate the report such as used and unused medical products for each medical procedure and add-on medical products.

The electronic storage device 205 may also include credentials 345 and Data and Insights Platform 350 (also referred to herein as Platform). In accordance with aspects of the disclosure, different users may access different information and screens in the Platform on a client device (such as a client device in a hospital 24 or manufacturer 26). The authorized user may be based on job description (from the hospital information) and location of access (whether at the manufacturer 26 or hospital 24). The credentials 345 may include a user name and password and associated assess right for the user. For example, a nurse may have different access rights than a materials manager. The manufacturer 26 may also have different access rights than the materials manager. The Platform 350 includes template information for displaying the various screens.

When there are more than one first type of dispensers (e.g., multiple kiosks 16), each first type of dispenser may have different medical products. The first type of dispensers may be located at the same location in a building, at multiple locations within one building, or at multiple locations in multiple buildings.

The electronic storage device 205 may also store a product catalog of available medical products from the manufacturer 26.

Figure 4A:
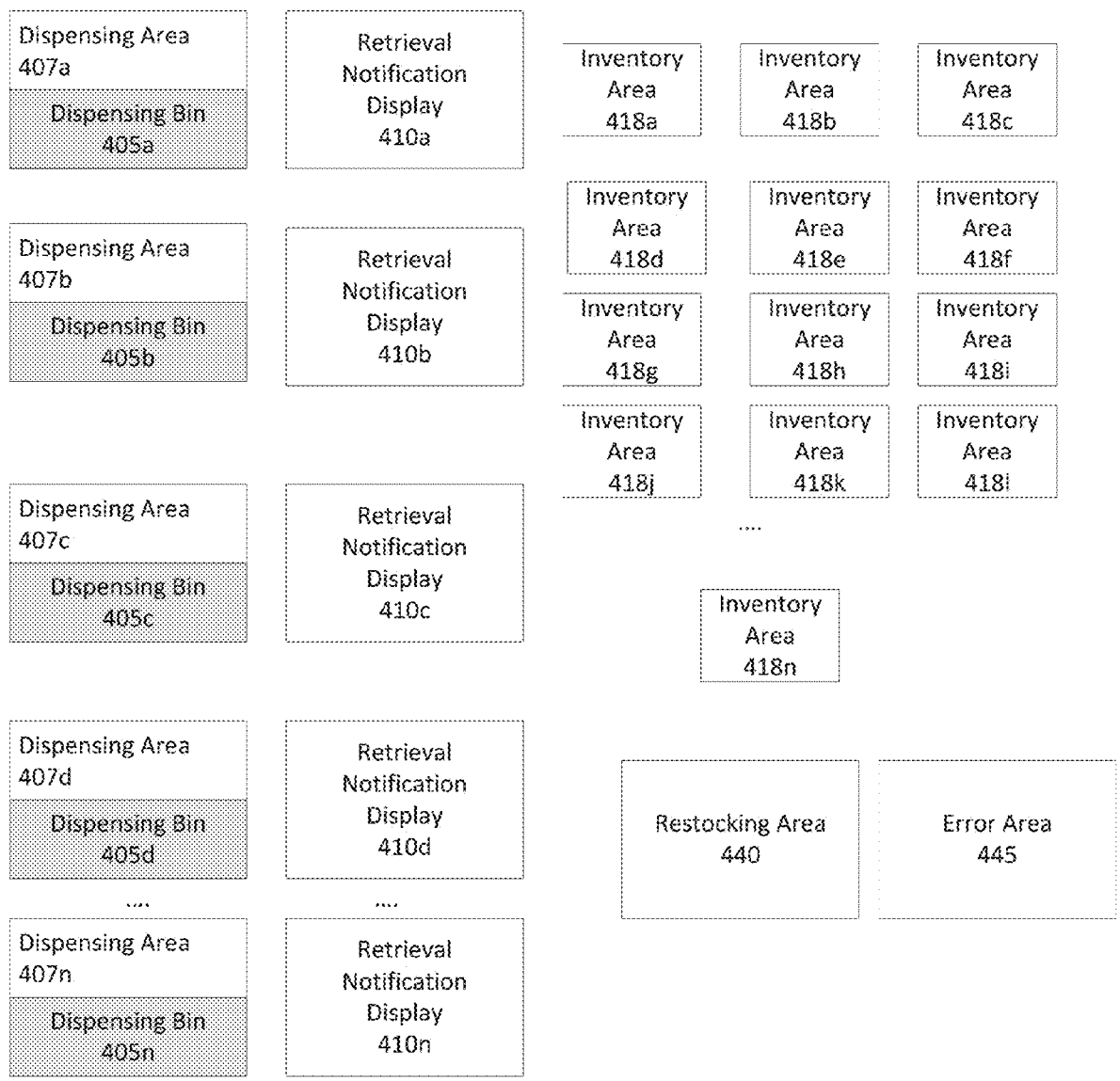
FIGS. 4A and 4B are block diagrams of an example of a first type of dispenser in accordance with aspects of the disclosure.
Figure 4B:
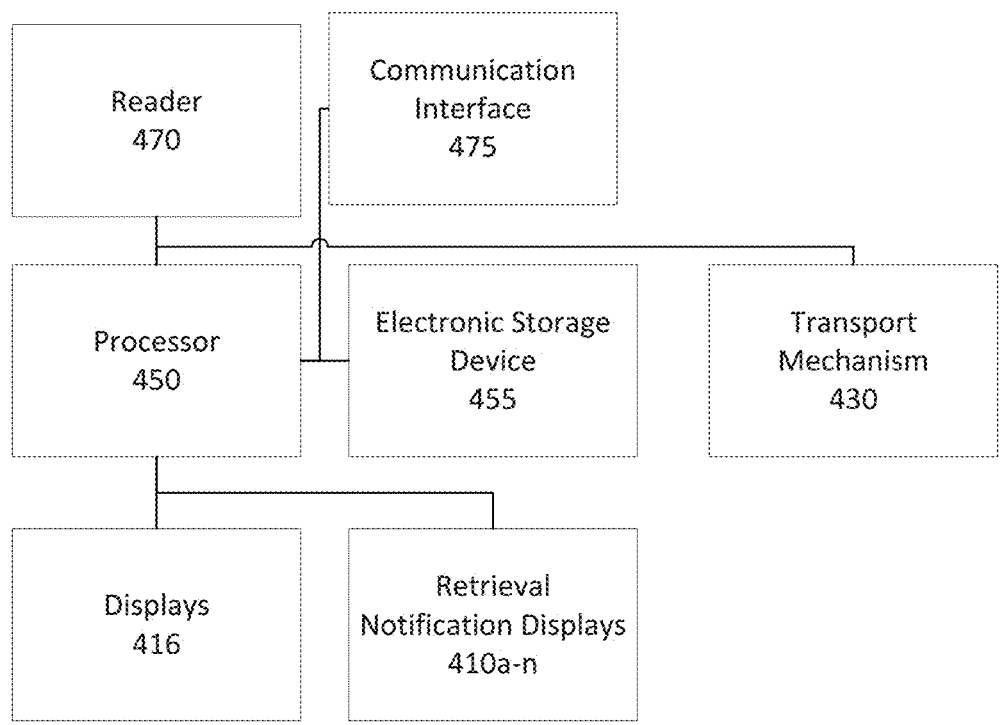

FIGS. 4A and 4B are block diagrams of an example of a first type of dispenser (e.g., Kiosk 16) in accordance with aspects of the disclosure. The first type of dispenser has a plurality of dispensing areas 407*a-n*. In an aspect of the disclosure, the number of dispensing areas 407*a-n* may be determined based on a size of a core, a size of a hospital. Each dispensing area 407 may have a shelving system. Each dispensing area may have a corresponding dispensing bin 405*a-n*. A dispensing bin 405*a-n* may be a tray, a container and may be of various shapes and sizes. The dispensing areas 407*a-n* may be covered by an openable door, respectively, which are configured to open and provide access to a respective dispensing area.

Each dispensing area may have a corresponding retrieval notification display 410*a*-410*n*. In some aspects, the display 410*a*-410*n* may be adjacent to the corresponding dispensing area 407*a-n*.

Each of the retrieval notification displays 410*a*-410*j* can be any suitable display, such as a suitable liquid crystal display (LCD) and a light emitting diode (LED) display. Each of the retrieval notification displays 410*a*-410*n* can display various information, such as the name of the surgeon to which the medical products are to be dispensed, the type of procedure(s) that are to be performed with the dispensed medical products, a list of the medical products that are to be dispensed into the respective dispensing area 407*a-n*, the location within the facility the medical products that are to be dispensed are scheduled to be used, and/or the time the procedure(s), for which the medical products are to be dispensed, is scheduled to begin.

Each of the retrieval notification displays 410*a*-410*n* can include a button (shown as a circle on each of the retrieval notification displays 410*a*-410*n*), which is configured to receive a response from a user. The response is selected from the group consisting of an input force from a user, an input contact from the user, and/or an input of near physical contact within a predetermined proximity. The processor 450 then determines that the medical products in the dispensing area behind one of the openable doors 408*a*-408*n* is no longer stored within the first type of dispenser (e.g., kiosk 16) and is to be removed from the available inventory.

Each button on each of the retrieval notification displays 410a-410n can include a light source that can be configured to change color for example from red, to yellow, to green, upon receipt of a signal to indicate various messages, such as whether the total number of medical products of the pick list are dispensed. For example, each button can be red (which can indicate that the dispensing area 407a-n is not in use or can indicate that not all medical products of the pick list are in the dispensing area, each button can be green (which can indicate all medical products of the pick list are in the dispensing area, or each button can be yellow (which can indicate that an error has occurred, or that at least one of the medial products in the dispensing area is different from the medical product of the pick list, or that some but not all medical products are ready for pick up).

One of the buttons corresponding to a retrieval notification display 410a-410n can receive a response from a user. This may be a way that the processor 450 determines that a dispensing bin may be available.

Receipt of the response by the button of the retrieval notification display 410a-410n is also acknowledged and stored within an electronic storage device 455, transmitted via communication interface 475 and/or stored within a server 10.

Thus, a processor 450 controls the color of the button of the retrieval notification display 410a-410n, and if further medical products are to be dispensed, begin to move medical product(s) stored within the first type of dispenser to the dispensing bin 405a-n.

The first type of dispenser may also include an error area 445 such as a bin (container).

Medical products can be moved to the error area 445 for one of several reasons. For example, medical product(s) can be placed in the error area since they are, upon a scanning, acknowledged as being expired (or within a threshold amount of time before expiration). As another example, upon return of medical product(s) that have previously been dispensed, those returned medical product(s) may be damaged, or may be incapable of being scanned with a reader. As another example, upon return of medical product(s) that have previously been dispensed, those returned medical product(s) may be identified as not being the same as any other medical products within the first type of dispenser. As another example, the first type of dispenser can receive data from the server 10 indicating that a certain type of medical product(s) have been recalled, upon receipt of such data, the first type of dispenser can then cause those medical product(s) to be moved from an inventory area into the error area 445.

In each example above of a medical product being moved to the error area 445, a communication interface 475, under the controller of the processor 450 can be configured to transmit to a server 10, a signal that an error is determined and/or the medical product is in the error area 445 (with identifier and quantity).

The first type of dispenser may also include a door covering the area error (door not shown).

In an aspect of the disclosure, the first type of dispensers may have one or more displays 416. These displays 416 may be touchscreens. In some aspects of the disclosure, the displays may be a graphical user interface (GUI). One of the displays may be an error notification display.

The display 416 can be configured to receive an input contact from a user, wherein the contact is used to receive a code (such as an access code so that a user can open one or more doors of the first type of dispenser), and receive signals from the electronic storage device 455. The display 416 can also display data selected from the group consisting of a number of each of the plurality of medical products within the dispenser, a location of each of the plurality of holders, and which medical product of the plurality of medical products is stored in each of the plurality of holders.

The input from the user received by the display 416 can be a specific medical product(s) to be dispensed from first type of dispenser can be selected through a user's interaction with the display 416. In other aspects, the display 416 can list an inventory of all medical products within the first type of dispenser. In other aspects, the display 416 can provide an illustration of all medical products within first type of dispenser, so that a user can select the desired medical product.

Further, in other aspects, the processor 450 can receive a transmitted request to dispense a specific medical product through an internet connection. This transmitted request can come from any other user or device that is configured to transmit request through the internet connected first type of dispenser (e.g., directly from a client device). After dispensing, the processor 450 may notify the server 10 regarding the type and quantities dispensed to update the inventory.

The display 416 allows a user to interact with the first type of dispenser in any suitable way. For example, a user can access the display 416 by first scanning an identification card with a reader 470 and/or entering a passcode.

The display 416 may also present alternative medical product(s) to those selected, and show a comparison between the selected medical product and the allowable substitute medical product. The list of allowable substitute medical products may be received from the server 10. Also, the display 416 can be used to order further stock of one or more medical products.

The display 416 can also accept a request directly (or through receiving a transmitted request) to have specific medical product(s) on an inventory area.

The first type of dispenser also includes a plurality of inventory areas 418a-n each of which are configured to store one or more medical products in fixed locations within the dispenser 400. Each of the plurality of areas 418 is configured to maintain one or more medical products in a fixed location, so that a plurality of medical products can be stacked on top of each other within each of the plurality of areas 418a-n. Each of the plurality of areas 418a-n can be the same size, so that the stored medical product is the same size for each areas 418a-n, or the plurality of areas 418a-n can be varied sizes so that medical products of different sizes can be stored therein.

In some aspects, the areas 418a-n may include holders or cassettes to hold the medical products. Each of the holders can completely surround the circumference of each of the medical products, or one or more holders can include a slot, so that a portion of a medical product stored within the holder can be visible and/or accessible.

Each area 418 includes a plurality of medical products, which are stacked on top of each other vertically within the area. The number of medical products stored with each area 418 can vary, from a single medical product to tens or hundreds stacked vertically on top of each other. Also, each individual area 418 may contain the same kind of medical product as one or more of the other individual area 418 within the first type of dispenser, or each individual area 418 stores a unique medical product that no other holder stores.

The number of rows and number of columns of areas may be based on the size of the core or hospital where the dispenser is located.

The first type of dispenser may also include a restocking area 440 which receives medical products to be restocked into one or more inventory areas 418*a-n*.

Medical products may be moved from one or more inventory areas 418*a-n* to one or more dispensing bins 405*a-n* or from the restocking area 440 to one or more inventory areas 418*a-n* or from the one or more inventory areas 418*a-n* to the error area 445 via one or more transport mechanism 430 under the control of a processor 450.

In some aspects, each row of inventory areas has a transport mechanism 430. Each transport mechanism 430 may include a reader configured to scan an identifier on the medical product. Because the medical products are stacked vertically on top of each other, the reader of the transport mechanism 430 is configured to read the identifier on the medical product vertically highest within the inventory area 418, upon reading the identifier, move the vertically highest medical product within the inventory 418 to a dispensing bin 405 (or error area 445). When the identifier is read, it may be stored in the electronic storage device 455 (and subsequently transmitted to the server 10).

In some aspects of the disclosure, the transport mechanism 430 may include a railing system, one or more motors, a head with a reader. The railing system allows the head to move within the first type of dispenser. The one or more motors move the head along the railing system. The head is configured to obtain the medical product (inventory or restock) after scanning by the read and move the medical product to the appropriate location. For example, the head may apply a negative pressure through a cup that extends from the lower surface of the head, when the cup contacts or nearly contacts the medical product (inventory or restock), causing the medical product to be secured to the cup of the head. The cup can be any suitable shape and structure, and can be formed of any suitable pliable, rigid or semi-rigid material. A vacuum or any other suitable mechanism can provide the negative pressure to the head. The reverse occurs when the transport mechanism 430 is located at the appropriate location (inventory area 418*a-n* or dispensing bin 405*a-n*), e.g., stopping the negative pressure to released the medical product. In an aspect of the disclosure, the appropriate location is determined by an inventory map or planogram stored in the electronic storage device 455 or location received from the server 10.

In an aspect of the disclosure, the first type of dispenser receives a notification from the server 10 to expect a restocking of medical products. The notification may include the identifier of the medical product and quantity. In other aspects, the notification may also include the expiration date. In other aspects, the notification may also include if the product has been recalled. In response to receiving this notification, the first type of dispenser may enter restock mode. The processor 450 may cause the controls the transport mechanism 430 to move over the restocking area 440 and to attempt to read/scan a medical product. If no medical product is scanned, the processor 450 may repeat this process until a medical product has been scanned or until a predetermined period has expired.

In other aspects of the disclosure, instead of receiving the notification, the first type of dispenser periodically checks whether a medical product is placed in the restocking area 440. The processor 450 controls the transport mechanism 430 to move over the restocking area 440 and to attempt to read/scan a medical product. If a medical product is read, the processor 450 determines that there is a medical product for restocking. In other aspects of the disclosure, the first type of dispenser checks whether there is a medical product in the restocking area 440 after completing dispensing medical products for all pick lists received. In other aspects of the disclosure, the first type of dispenser checks whether there is a medical product in the restocking area 440 after the replenishment mode is finished. In other aspects of the disclosure, the first type of dispenser checks whether there is a medical product in the restocking area 440 when a door (not shown) covering the restocking area 440 is closed.

In yet another aspect of the disclosure, the first type of dispenser has a sensor to detect when a medical product is placed in the restocking area 440 or when a door covering restocking area 440 is opened and then closed. The sensor reports a detection result to the processor 450. The processor 450 may activate a flag and the processor 450 controls the transport mechanism 430 to move over the restocking area 440 and to attempt to read/scan a medical product. The processor 450 may check the restocking area 440 as long as the flag is activated. Once all medical products are restocked, the flag may be deactivated.

The sensor in the restocking area 440 may be a pressure sensor. In other aspects, the sensor may be a light detector (transmitter/receiver) and when the medical product is placed in the restocking area 440, the light transmitter is blocked and not received by the receiver. In other aspects, the restocking area 440 may have a scale and when any weight is detected, the detection is reported to the processor 450.

In an aspect of the disclosure, the processor 450 may be CPUs. The processor 450 may be a single core or multiple core processor. In other aspects, some of the processor 450 may be GPUs. In other aspects, the processor 450 may be integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Electronic storage device 455 can include computer system readable media in the form of volatile memory, such as random access memory (RAM) and/or cache memory or others. In some aspects, multiple electronic storage devices 455 may be used. The electronic storage device 455 may be any type of integrated circuit or other storage device adapted for storing data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

In an aspect of the disclosure, the electronic storage device 455 may include an inventory map including the quantities of each type of medical device(s) in the inventory areas (designated by the planogram). In some aspects of the disclosure, the processor 450 may update the inventory map by subtracting a removed medical product when the reader in the transport mechanism reads the medical product. In other aspects of the disclosure, the processor 450 may transmit the read identifier to the server 10 and the server 10 performs the subtraction.

In an aspect of the disclosure, the first type of dispenser has a plurality of operation modes. The modes include, but are not limited to recall, replenishment, job picking (dispensing), restocking and maintenance. In some aspects of the disclosure, the different modes have priority over another mode. For example, job picking (dispensing) medical products for a pick list received from the server 10 to a dispensing bin 405 has priority over restocking an inventory area 418 from the restocking area 440. Accordingly, when a new pick list (scheduled medical procedure) is received from the server 10, the processor 450 may cause the transport mechanism to complete a current restocking of a medical product which is already scanned and then stop restocking and change the operation mode to job picking (dispensing).

In some aspects, replenishment has priority over job picking (dispensing) medical products for a pick list received from the server 10 to a dispensing bin 405. Similarly, when the first type of dispenser is put into a replenishment mode, the processor 450 may cause the transport mechanism to complete a dispensing of a medical product which is already scanned to a dispensing bin 405 and then stop.

The first type of dispenser may also have a reader 470 (such as a bar code reader, a QR code reader, a Radio Frequency Identification (RFID) reader, etc.) to read a box of medical devices for replenishing an inventory area 418. In FIG. 4B, a communication bus (bus) is not specifically labeled.

In an aspect of the disclosure, the communication interface 475 is a wireless communication interface. In other aspects of the disclosure, the communication interface is a wired communication interface.

In an aspect of the disclosure, the first type of dispenser may periodically receive a polling from the server 10 for its status request. The processor 450 via the communication interface 475 transmits a heartbeat response. The heartbeat includes at least the status, e.g., online and powered or error.

FIG. 5A illustrates a block diagram of one example of a second type of dispenser such as hub 16. The second type of dispenser has exterior walls. The shape of the dispenser may be customized as need for a particular location. In an aspect of the disclosure, the dispenser may have a generally rectangular shape. In some aspect, the height may be larger than the width. The second type of dispenser has a plurality of dispensing areas 518a-n and a display 516. In an aspect of the disclosure, some of the dispensing areas may be above the display and other of the dispensing areas may be below the display. The number of dispensing areas 518a-n and arrangement of the dispensing areas 518a-n may be determined based on a size of a hospital 24 where the dispenser is located.

In an aspect of the disclosure, each dispensing area 518 may have a holder 519. FIG. 5B illustrates a block diagram of a dispensing holder 519. Each of the plurality of holders 519 being configured to store at least one of the plurality of medical products in a fixed location. That fixed location is associated with the kind of one of the plurality of medical products, and each of the plurality of holders 519 comprising a dispensing opening 520.

Each of the plurality of holders 519 can be the same size, so that the stored at least one medical product is the same size for each holder 519, or the plurality of holders 519 can be varied sizes so that medical products of different sizes can be stored therein.

Figure 5C:
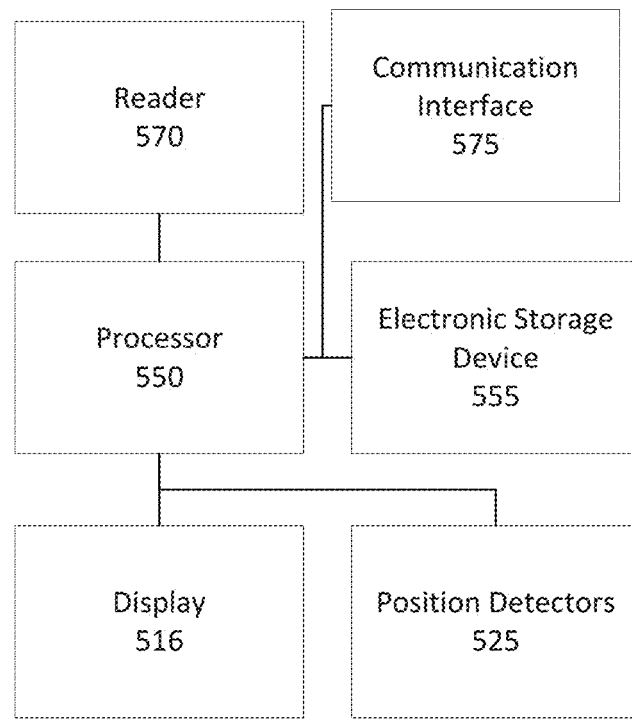

FIG. 5C illustrates a block diagram of additional elements of the second type of dispenser such as the hub 18. The second type of dispenser includes position (location) detectors 525. The position detectors 525 are configured to detect the position of a medical product which is dispensed. In FIG. 5C, a communication bus (bus) is not specifically labeled.

In an aspect of the disclosure, there are at least two detectors 525 mounted perpendicular to each other. Each position detector 525 may comprises an emitter and a sensor. The at least two emitters and at least two sensors may be placed around a periphery of the dispenser creating the boundaries of an imaginary plane that is substantially perpendicular to the dispensing openings 520 of the holders 519. For example, the emitters and detectors may be mounted on a wall of the second type of dispenser, such as a front edge of the walls.

As used herein, the emitter refers to any circuit or device that may be used to create an electromagnetic field or emission, e.g., an electric field, magnetic field, light or light energy. An emitter may include one or more combinations of emitters in a single or in separate emitters. As used herein, the term "light" or "light energy" is used generically to refer to electromagnetic radiation, and so the term includes, for example, visible, infrared and ultraviolet radiation. Any suitable type of emitter may be used, but in some aspects, the emitter is a light-emitting diode (LED). In some aspects, an emitter emits light at a particular wavelength. In other embodiments, a single emitter may emit light at a first wavelength and a second wavelength, or more than three wavelengths.

In an aspect of the disclosure, each emitter may transmit multiple lines of light by rotating the emitter beam. In this aspect, the processor 450 may receive the beam angle from the emitter. In other aspects, the emitter is directional and only transmits one beam in a fixed direction. The plurality of lines produced by the emitters form the plane, which was mentioned above.

As used herein, the sensor is configured to detect light from one, two or more of the emitters, and this detected light generates a signal. The signal is sent to the processor 550. Any suitable detector capable of detecting light, such as a photodetector, may be used for sensor. Examples of photodetectors include photodiodes, photoconductive cells, photoresistors, phototransistors, light to digital converters, and the like.

The detectors are used to determine an x and y position (in the plane).

In an aspect of the disclosure, the processor 550 may be CPUs. The processor 550 may be a single core or multiple core processor. In other aspects, some of the processor 550 may be GPUs. In other aspects, the processor 550 may be integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Electronic storage device 555 can include computer system readable media in the form of volatile memory, such as random access memory (RAM) and/or cache memory or others. In some aspects, multiple electronic storage devices 555 may be used. The electronic storage device 555 may be any type of integrated circuit or other storage device adapted for storing data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

In an aspect of the disclosure, the electronic storage device 555 may include an inventory map including the quantities of each type of medical device(s) in the inventory areas (designated by the planogram). The inventory map may contain the identifier of the medical product and/or the location identifier. The electronic storage device 555 may also store the location of each of the plurality of dispensing openings 520 within the dispenser 100. In an aspect of the disclosure, the stored location for the openings includes the x and y position. The stored location is associated with its corresponding holder 519 (e.g., inventory area).

In an aspect of the disclosure, the holder 519 may be removably mounted in the inventory area 518.

The dimensions of the dispensing opening 520 can be adjusted. For example, in an aspect of the disclosure, the height of the dispensing opening 520 can allow for removal of a single medical product from the holder 519. Although not shown, the plane discussed above would be substantially parallel with the front surface of the holder 519, so that the front surface and the plane are substantially perpendicular to the dispensing opening 520, and substantially perpendicular to the path a medical product moving through the dispensing opening 520 would take.

The processor 550 can receive input from the sensors in the detectors 525, and the processor 550 is configured to determine if one of the plurality of medical products dispensed. The processor 550 can make this determination because, based on the input from the at least two sensors in the detectors 525, the processor 550 can determine the location of the dispensing opening 520 along both the x axis and the y axis. The processor 550 compared the determined position with the stored position. When there is a match, the processor 550 determines the corresponding inventory area and can report either the location identifier or medical product identifier to the server 10.

The processor 550 can receive an input from the position detector 525 when a leading edge of a medical product has moved to and past the plane formed by the emitter and detector, and/or the processor 450 can receive an input from the position detector 525 when a trailing edge of the medical product has moved to and past the same plane. If only a leading edge is determined as moving to and past the plane, the medical product is not considered removed since the medical product was only partially moved through the dispensing opening 530, and likely was pressed back into the holder 519. If the trailing edge is determined as moving to and past the plane, the medical product is considered removed and the available inventory can be updated. While in the holder 519, the leading edge is closer to the front of the dispenser such as a dispensing opening than the trailing edge.

In other aspects of the disclosure, each opening may have its own detector.

The second type of dispenser such as the hub 18 may have a reader 570 (such as a bar code reader, a QR code reader, a Radio Frequency Identification (RFID) reader, etc.). When one or more medical products are added to the dispenser, through a replenishment process, a user carries one or more new medical products to the dispenser. The reader 570 reads the identifier of the medical product and/or the box containing a plurality of medical product. The information conveyed by the scanning may be stored in the electronic storage device 555 (e.g., type, quantity and expiration date). Additionally, in an aspect of the disclosure, the processor 550 may transmit the information to the server 10 via its communication interface 575. In response, the server 10 updated the second type dispenser information 330 (for the corresponding hub).

The reader 570 can be on any portion of the second type of dispenser such as a hub 18 that is accessible by a user, which is also configured to scan the identifier of the new medical product. Alternatively, or in conjunction, the user can interact with a display 516 and manually enter the number and type of new medical product to be added.

The communication interface 575 may be a wireless communication interface. In other aspects, the communication interface may be a wired interface.

In an aspect of the disclosure, the second type of dispenser may periodically receive a polling from the server 10 for its status request. The processor 550 via the communication interface 575 transmits a heartbeat response. The heartbeat includes at least the status, e.g., online and powered or error.

The processor 550 can also receive a recall request. The recall request is a list of one or more medical products of the plurality of medical products have been recalled for any reason. To avoid the possibility that the medical products may be removed from the second type of dispenser, the display 516 can display a warning that a certain medical product has been recalled, and/or the display 516 can display a warning, upon removal of a medical product that has been recalled, that the just removed medical product has been recalled.

In other aspects of the disclosure, the second type of dispenser may receive an available inventory request from the server 10. In an aspect of the disclosure, the available inventory is inventory (for the type) received by replenishing minus dispensed inventory (for the type). The processor 550 transmits a response to the request via the communication interface 575 to the server 10.

Additionally, the second type of dispenser may receive an updated inventory map from the server 10. The processor 550 stores the updated inventory map in the electronic stored device 555.

The display 516 can be a graphical user interface (GUI), and is included on a front surface of the second type of dispenser such as hub 18. In other aspects, the display 516 can be in any other suitable location on the second type of dispenser. The display 516 is configured to receive an input from a user, receive signals from the processor 550, and display data. The input received from a user is selected from the group consisting of an input force from a user, an input contact from the user, and/or an input of near physical contact within a predetermined proximity, each of which can be used to make a selection, and/or alter what is being displayed on the display 516.

This data the display 516 is capable of displaying can be selected from the group consisting of a number of each of the plurality of medical products within the second type of dispenser (such as hub 18), a planogram of the plurality of dispensing areas 518 and their associated at least one of the plurality of medical products, and which holder 519 is associated with the replenished medical product. Also, the display 516 can indicate which holders 519, for example, by displaying "The medical product just scanned is to be placed in holder XX".

Figure 6A:
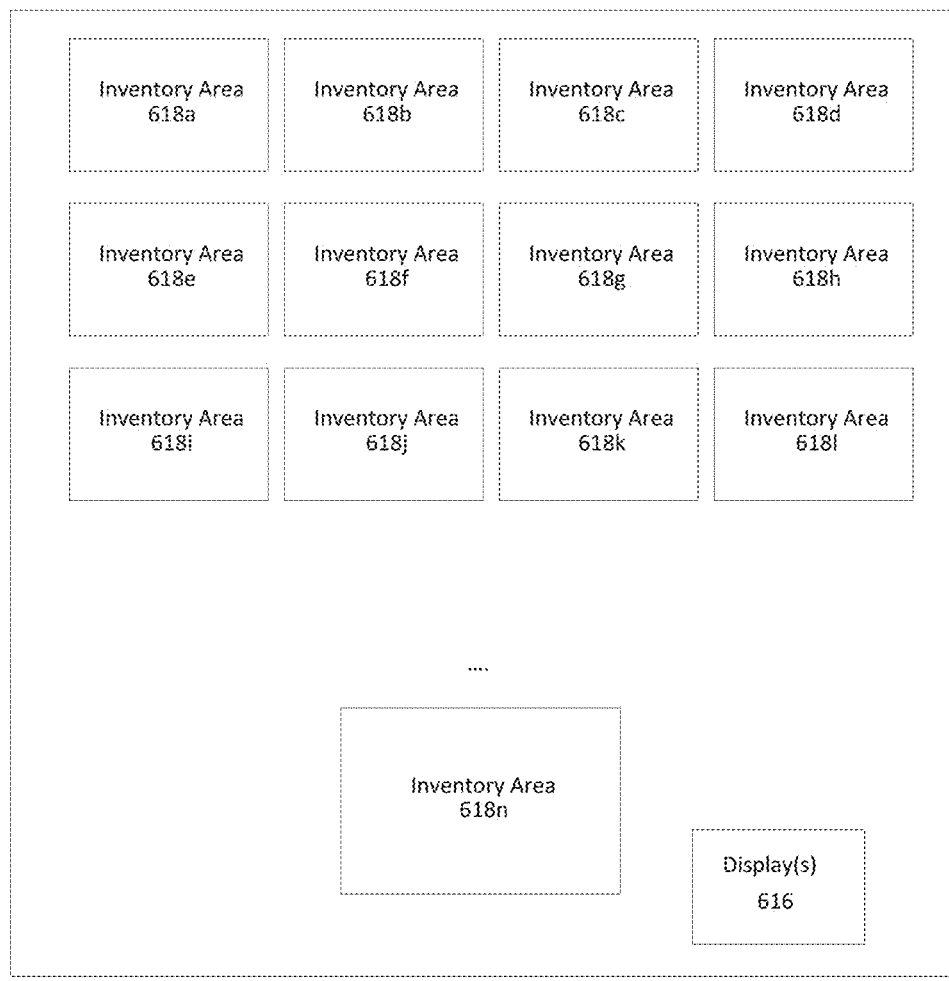
FIG. 6A-6C illustrates another example of a second type of dispenser in accordance with aspects of the disclosure.
Figure 6B:
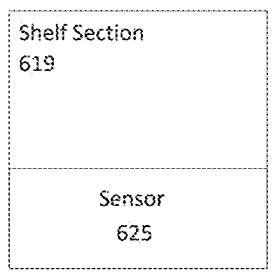
Figure 6C:
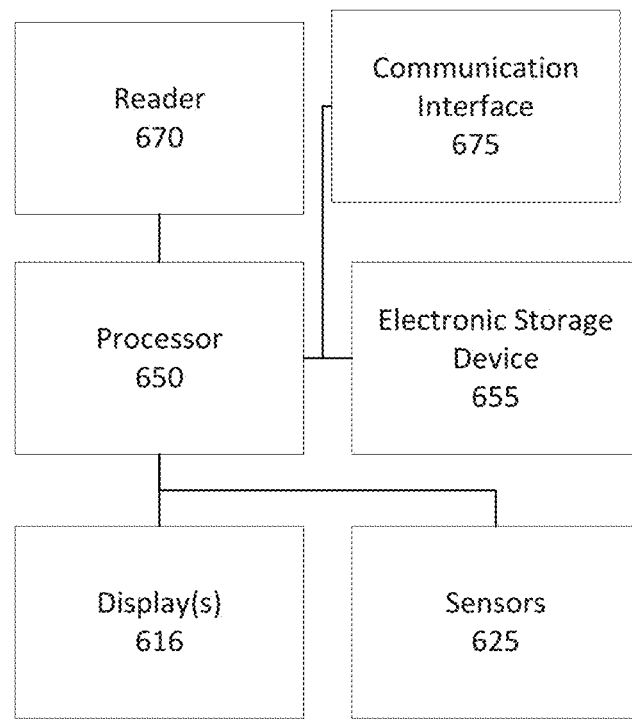

The display 516 can also be configured to receive an input from a user, wherein the input is used to receive a code (such as an access code so that a user can replenish medical products without creating an alarm). In an aspect of the disclosure, the display 516 may receive input of data relating to the manually removed medical products such as an operating room number and/or scheduled time of the medical procedure and/or the identifier of the scheduled medical procedure. For example, the display 516 may display a plurality of operating room numbers for selection. This information may be transmitted to the server 10 and used to associate the manually removed medical products to a scheduled medical procedure. FIGS. 6A-6C illustrate block diagrams of another example of a second type of dispenser, e.g., Smart Shelves 20. The Smart Shelves 20 also similar to the hub 18 in that medical products may be manually removed from the dispenser. In an aspect of the disclosure, the Smart Shelves 20 may be located outside of the operating room 22 but within a core of operation rooms. In an aspect of the disclosure, the Smart Shelves 20 may dispense medical products not dispensed from a first type of dispenser (e.g., Kiosk 16). In an aspect of the disclosure, the hub 18 may dispense the same medical products as the first type of dispenser (e.g., Kiosk 16).

The Smart Shelves 20 may be larger than the hub 18 and may dispense medical products that are larger in size. As with the other dispensers, the Smart Shelves 20 may have a plurality of dispensing areas 618. Each dispensing area 618 may include a shelf section 619. In some aspects of the disclosure, a holder may be placed on top of the shelf section 619. In other aspects of the disclosure, a medical product may be directly placed on the shelf section 619. In this aspect, the Smart Shelves 20 may have vertical dividers between the shelf sections 619.

In an aspect of the disclosure, each shelf section 619 has a sensor 625. The sensor 625 is configured to detect a placement of a medical product on the shelf section 619 or removal of a medical product from the shelf section 619. The sensor 625 may be a weight sensor. The weight sensor may be a pressure sensor such as a pressure transducer or a strain gauge. During a calibration or a configuration stage, a medical product for the shelf section 619 may be placed on the sensor 625 such that a reading may be recorded in the electronic storage device 655. This reading represents the weight of a single medical. Since different medical products may have different weights, a reading may be taken for each type of medical product and the reading associated with a specific location identifier. Each shelf section 619 (and inventory area 618) may be defined in the electronic storage device 655 by its location identifier and medical product identifier. In an aspect of the disclosure, as will be detailed later, a planogram may be received from the server 10 which include the location identifier and the medical product identifiers.

Medical Products may be added, either via replenishment (new medical products) or restocking (previously dispensed medical product) one or more at a time. The quantity of added medical products may be determined by calculating the change in the reading from the sensor 625 (from a previous stored reading) and determine a relationship between the same and the value of the initial reading for one medical product. Each time the reading changes, the reading may be stored in the electronic storage device 655. In an aspect of the disclosure, a processor 650 receives the reading, e.g., sensed value, from the sensor 625 and retrieves the corresponding initial reading from the electronic storage device and determines the quantity of added medical products. The processor 650 may update the inventory map in the electronic stored device 655 with the added medical products for the corresponding type.

In other aspects of the disclosure, the processor 650 may receive the reading, e.g., sensed value, from the sensor 625 and transmit the reading itself and the location identifier and/or medical product identifier via a communication interface 675 to the server 10. In this aspect, a processor 200 in the server 10 determines the quantity added and updates the inventory (inventory map) for the corresponding type. Additionally, in this aspect of the disclosure, the initial reading from each sensor 625 may be transmitted via the communication interface 675 to the server 10 at installation. In this aspect of the disclosure, the server 10 subsequently transmits the updated inventory map to the processor 650 for storage in the electronic storage device 655.

Similarly, one or more medical products may be dispensed, e.g., removed, from an inventory area 618 (shelf section 619). The quantity of removed medical products may be determined by calculating the change in the reading from the sensor 625 and determine a relationship between the same and the value of the initial reading for one medical product. In an aspect of the disclosure, a processor 650 receives the reading, e.g., sensed value, from the sensor 625 and retrieves the corresponding initial reading from the electronic storage device and determines the quantity of removed medical products. The processor 650 may update the inventory map in the electronic stored device 655 with the removed medical products for the corresponding type.

In other aspects of the disclosure, the processor 650 may receive the reading, e.g., sensed value, from the sensor 625 and transmit the reading itself and the location identifier and/or medical product identifier via a communication interface 675 to the server 10. In this aspect, a processor 200 in the server 10 determines the quantity removed and updates the inventory (inventory map) for the corresponding type (second type inventory information 335).

Additionally, in this aspect of the disclosure, the initial reading from each sensor 625 may be transmitted via the communication interface 675 to the server 10 at installation. In this aspect of the disclosure, the server 10 subsequently transmits the updated inventory map to the processor 650 for storage in the electronic storage device 655.

In other aspects of the disclosure, different sensors or detectors may be used. For example, the location detector as described for hub 18 may be used to determine a position of adding or removal.

In an aspect of the disclosure, the Smart Shelves may also comprise a reader 670 (such as a bar code reader, a QR code reader, a Radio Frequency Identification (RFID) reader, etc.) and one or more displays 616. The reader 670 may scan a box of new medical products prior to insertion of a shelf section 619. Similar to above, after the reader 670 scans the medical products, the processor 650 may transmit to the server 10, the identifier of the box (which conveys quantity and expiration date). In this aspect of the disclosure, the sensor 625 may be used to confirm that the entire box was added to the shelf section 619. In other aspects, this reading may be used as a baseline for reference to adding or dispensing medical products. In response to receiving the identifier of the box of medical products or the other information from the processor 650, a processor 200 in the server updates the inventory map (second type inventory information 335). The displays 616 may be the same type as described above and may display any of the information described above, including a list of operating rooms.

The reader 670 can be on any portion of the second type of dispenser such as a Smart Shelves 20 that is accessible by a user, which is also configured to scan the identifier of the new medical product. Alternatively, or in conjunction, the user can interact with a display(s) 616 and manually enter the number and type of new medical product to be added.

The communication interface 675 may be a wireless communication interface. In other aspects, the communication interface may be a wired interface.

In an aspect of the disclosure, the processor 650 may be CPUs. The processor 650 may be a single core or multiple core processor. In other aspects, some of the processor 650 may be GPUs. In other aspects, the processor 650 may be integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In FIG. 6C, a communication bus (bus) is not specifically labeled.

Electronic storage device 655 can include computer system readable media in the form of volatile memory, such as random access memory (RAM) and/or cache memory or others. In some aspects, multiple electronic storage devices 655 may be used. The electronic storage device 655 may be any type of integrated circuit or other storage device adapted for storing data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

In an aspect of the disclosure, the second type of dispenser such as the Smart Shelves 20 may periodically receive a polling from the server 10 for its status request. The processor 650 via the communication interface 675 transmits a heartbeat response. The heartbeat includes at least the status, e.g., online and powered or error.

In an aspect of the disclosure, each transmission from/to a dispenser may include a time stamp.

Figure 7:
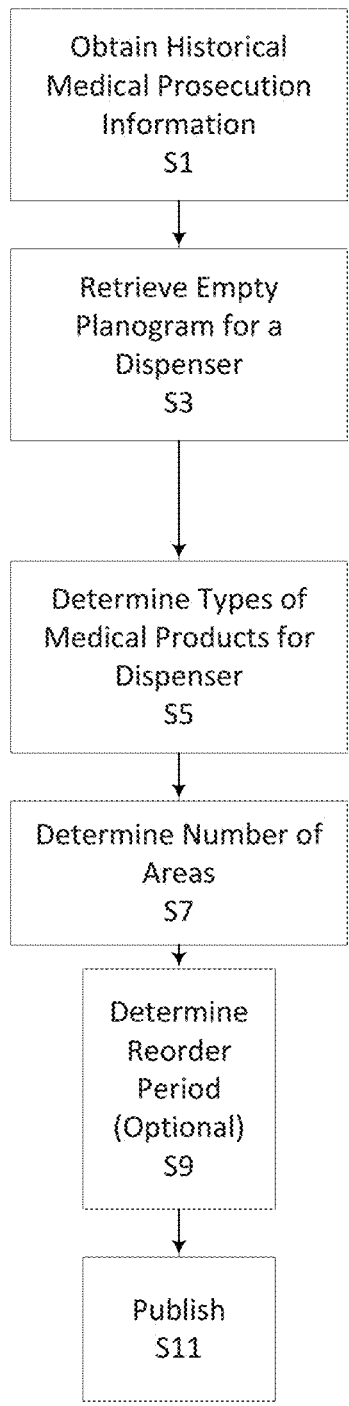
FIG. 7 illustrates a flow chart for determining a planogram for a dispenser in accordance with aspects of the disclosure.

FIG. 7 illustrates a flow chart for determining a planogram for each dispenser in accordance with aspects of the disclosure. At 51, a processor 200 in the server 10 obtains the historical medical procedure information 300. This information may be obtained in any manner, such as FTP, secure network transfer or pulling via a network. In other aspects of the disclosure, the historical medical information 300 may be transmitted by hospital personnel. The historical medical procedure information 300 may be divided by operating room or by core.

At S3, the processor 200 in the server 10 obtains an empty planogram for the dispenser. Each dispenser may have a different arrangement of inventory areas and thus a different planogram. The planogram comprises a plurality of inventory areas. The processor 200 may obtain the number of the inventory areas from the planogram. In an aspect of the disclosure, the height of the inventory areas may also be included. The height may be used to determine the number of medical products that can be stored in a given inventory area. The number of medical products that can be stored in a given inventory area may differ for different medical products. These inventory areas are arranged in rows and columns. However, the size of the rows and columns may vary and the size of the inventory areas may be different.

At S5 and S7, the processor 200 in the server 10 determines the types of medical devices and quantity of inventory areas for each medical device to be included in the respective dispenser. FIG. 7 shows them as separate blocks for descriptive purposes, however, the determination may be executed together. This is determined using the historical medical procedure information 300. In some aspects, the processor 200 may only use the historical medical procedure information relevant to the location of the dispenser. For example, if the dispenser is a first type of dispenser and will be located near a specific core, the processor 200 may only use the historical medical procedure information 300 for the operating rooms in the core. In some aspects, the processor 200 counts the number of medical procedures in the historical medical procedure information 300, determines an average quantity of medical products used per medical procedure, by type, a total of the medical products, by type, used in all medical procedures and average daily usage of the medical products, by type, and prioritizes medical procedures. For example, medical procedures that are more frequent may have a higher priority. In an aspect of the disclosure, a processor 200 in the server 10 counts the number of days included in the historical medical procedure information 300 using the dates of the medical procedures. In an aspect of the disclosure, the server 10 may receive a target replenishment period (cycle) from hospital personnel. In other aspects, the replenishment period may be a variable.

In an aspect of the disclosure, the planogram is determined to maximum procedure occurrences for a period of time (able to be dispensed), from the first type of dispenser subject to constraints. The occurrences may be a weighted, which is weighted by the priority. In an aspect of the disclosure, an occurrence is with respect to a specific provider and medical procedure (Provider-Procedure Pair). For example, when multiple providers are for a single medical procedure, there may be more than one occurrence for the medical procedure. In other aspects, the occurrence may be with respect to a medical procedure. A coverage used herein means a percentage of occurrences where a full set of requested medical products can be obtained from the dispenser versus total occurrences.

In an aspect of the disclosure, a processor 200 in the server 10 may optimize the types and quantity of inventory areas (for the type) using a plurality of binary variables to maximum occurrences (able to be fully dispensed) from the first type of dispenser (as weight). It is assumed that a small medical product can be placed in both small stack and large stack, while a large medical product can only be placed in the large stacks. In an aspect of the disclosure, it may be assumed that all occurrences of the Provider-Procedure pair are picked from the first type of dispenser (if the pair is selected).

The variables may include replenishment period, types of medical products, medical procedures, and provider. In the simulation, the replenishment period may be fixed by the hospital personnel. In an aspect of the disclosure, the types of medical products and medical procedures may be limited by the historical medical procedure information 300. A processor 200 in the server 10 iterative varies the plurality of variables to find the maximum occurrences able to be fully picked from the dispenser. In an aspect of the disclosure, a processor 200 in the server 10 may execute a commercial off the shelf optimization solver.

In an aspect of the disclosure, the optimization may account for allowable substitutes in the dispenser.

In other aspects, as shown in FIG. 7, the server 10 may also determine the replenishment period (cycle) at S9. The replenishment period (cycle) may be the replenishment period that achieves the maximum coverage (highest weighted occurrences picked from the dispenser).

A processor 200 in the server 10, once it determines the types of medical products and the number of inventory areas (for the product(s)), may assign a specific area to a specific type of medical products based on priority. In an aspect of the disclosure, different inventory areas may have different priorities. For example, inventory areas that are easier to retrieve the medical product(s) from and dispense the same may have higher priority. For example, an inventory area near the transport mechanism may take less time to dispense and have a higher priority. In an aspect of the disclosure, high usages medical products may be assigned to these higher priority inventory areas.

Once the planogram is populated with the identifiers of the medical products for each inventory area, the processor 200 in the server 10 publishes the planogram 305 in the electronic storage device 205. The planogram contains location identifiers associated with types of medical products, respectively. Any other processors in the server 10 will now have access to the planogram. Additionally, the client devices in the hospital and the manufacturer may also have access to the planogram 305. In an aspect of the disclosure, the determined maximum coverage may be provided to the material manager and/or other hospital personnel.

S3-S9 is repeated for each first type of dispenser.

In an aspect of the disclosure, since the system may provide 100% coverage for Provider-Procedure Pairs, the planograms for the second type of dispenser(s) may be determined to have a coverage of the balance of the Provider-Procedure Pairs. For example, if it is determined that the maximum coverage (weighted occurrences able to be fully picked from the first type of dispenser) is 80%, the planograms for the second type of dispenser are determined to cover the remaining 20% of Provider-Procedure Pairs.

Figure 8:
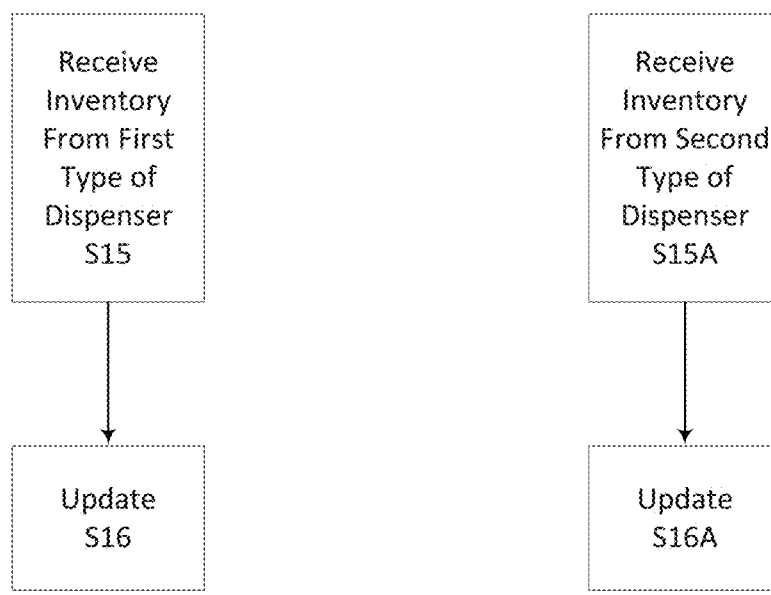
FIGS. 8A and 8B illustrate a flow chart for inventory replenishing in accordance with aspects of the disclosure.

In an aspect of the disclosure, the planogram for the smart shelves 20 may be set such that the remaining coverage may be obtained from the smart shelves 20 such that the hub 18 may contain the same medical products as the kiosk 16 (first type of dispenser) Each dispenser can receive new inventory of medical products. FIG. 8A illustrates a flow chart for replenishing a first type of dispenser. The first type of dispenser may be put in a replenishment mode. In an aspect of the disclosure, the server 10 may issue an instruction to the first type of dispenser when a replenish order has been issued to a material manager. The instruction may include information to be displayed on the display 416 for the user to see. For example, the information may be "place item A in Slot 3".

Once in a replenishment mode, a person such as a materials manager, a manufacturer, etc., may then open a door (door is not shown in FIGS. 4A and 4B) to the dispenser. Prior to insertion of the medical products into the inventory area(s), a box containing the medical products may be read by the reader 470 to read the identifier such as a Stock Keeping Unit (SKU). The box identifier indicates the type of medical device, quantity and expiration date. After the identifier of the box is read, the medical devices can be placed in the appropriate inventory area 418a-n. Also after the identifier of the box is read, the first type of dispenser may transmit the identifier to the server 10. In an aspect of the disclosure, the transmission may be at the time the heartbeat is transmitted. In an aspect of the disclosure, the first type of dispenser periodically transmits a heartbeat to the server 10. In this aspect, the identifiers of all boxes may be transmitted in aggregate. In other aspects, each time the box is read, the first type of dispenser may transmit the identifier to the server 10. In other aspects, the first type of dispenser may transmit the information when the dispenser changes modes of operation, e.g., from replenishment mode.

At S15, the server 10 receives the identifier(s) of the box(es) via the communication interface 210 and a processor 200 in the server 10 updates the electronic storage device 205. For example, since identifier of the boxes indicate the quantity of the medical products, a processor 200 in the server 10 adds the quantity to the inventory in the first type dispenser information 330 (for the corresponding type(s)) and the expiration date(s) at S16.

FIG. 8B illustrates a flow chart for replenishing a second type of dispenser.

At S15A, the server 10 receives the identifier(s) of the box(es) via the communication interface 210 and a processor 200 in the server 10 updates the electronic storage device 205. For example, since identifier of the boxes indicate the quantity of the medical products, a processor 200 in the server 10 adds the quantity to the inventory in the second type dispenser information 335 (for the corresponding type(s)) and the expiration date(s) at S16A. In an aspect of the disclosure, the server 10 may also receive the reading from the sensor(s) 625 in the Smart Shelves 20 and the location identifier and/or the identifier of the medical product from the processor 650 in addition to or in the alternative to the identifier of the box during replenishment.

Figure 9:
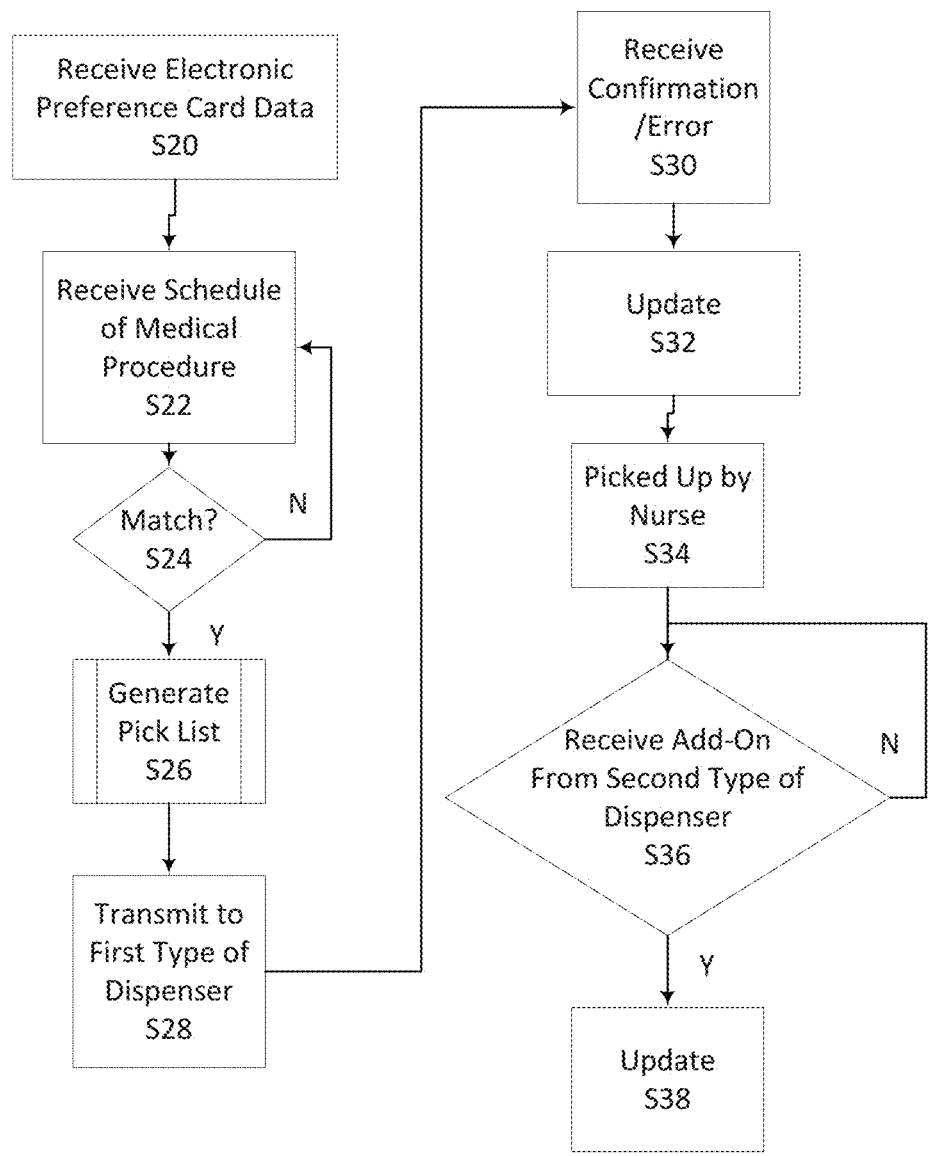
FIGS. 9-13 illustrate flow charts in accordance with aspects of the disclosure.
Figure 10:
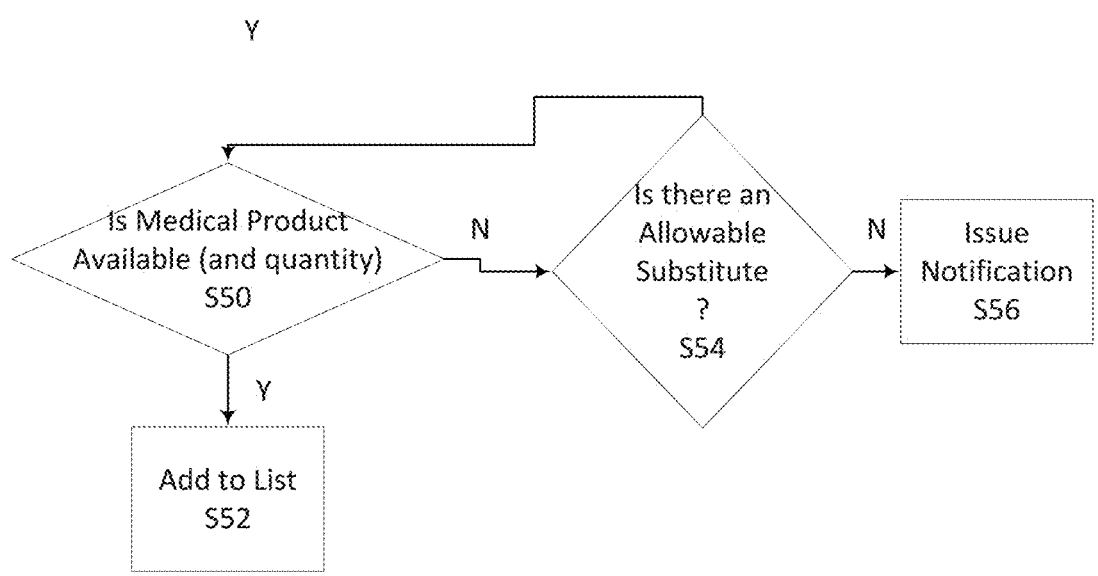
Figure 11:
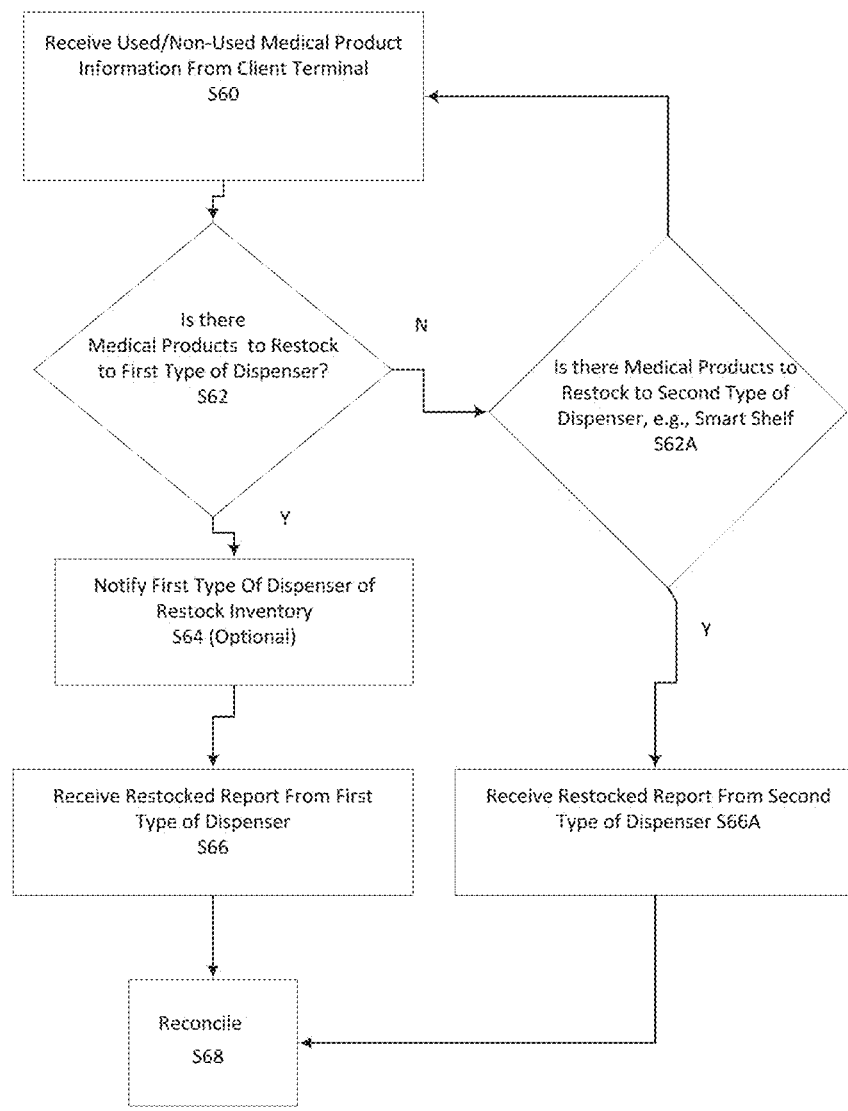

FIGS. 9-11 illustrate a method for dispensing medical products and inventory management in accordance with aspects of the disclosure.

At S20, the server 10 receives the electronic preference card data 310 from the client device 14. In an aspect of the disclosure, the server 10 may receive the electronic preference card data 310 respectively from a plurality of client devices 14 (different preference card data) (manually entered 2). A medical procedure may have multiple preference card data 310 (different surgeons). Additionally, the electronic preference card data 310 may be for different medical procedures. For each electronic preference card data 310, the data is stored in the electronic storage device 205. At the time of storage, the medical procedure may or may not be scheduled.

At S22, the server 10 receives a schedule of one or more scheduled medical procedures. The schedule may be sent daily, hourly or at other times. The schedule contains a list of all scheduled medical procedures for a period of time. In an aspect of the disclosure, when the schedule is received by the server 10, the medical procedures are deemed confirmed medical procedures. In other aspects of the disclosure, the server 10 may receive a separate confirmation of the scheduled medical procedures. The received schedule is stored in the electronic storage device 205 (315) by a processor 200 in the server 10. The schedule may be sent as a flat file. In other aspects of the disclosure, the server 10 may interface directly with a hospital scheduling system.

At S24, a processor 200 in the server 10 determines if a received electronic preference card data 310 matches a scheduled medical procedure. As described above, the electronic preference card data 310 may include an identifier of a medical procedure or an identifier of the provider and for each scheduled medical procedure; the schedule includes the identifier of the medical procedure and may include the identifier of the provider. The processor 200 examines the respective identifier(s) and determines if there is a match. When there is a match, a processor 200 in the server 10 generates a pick list for the medical procedure(s) (S26). When there is more than one electronic preference card data 310 for a single medical procedure, the server 10 may generate more than one pick list for the medical procedure. In other aspects, the server 10 may combine the electronic preference card data 310 into a single pick list.

FIG. 10 illustrates a flow chart for generating a pick list for a scheduled medical procedure. At S50, a processor 200 in the server 10 determines if one of the medical products included in the electronic preference card data 310 for the scheduled medical procedure is available in first type of dispenser (nearest the core or operating room) for the scheduled medical procedure. In an aspect of the disclosure, a processor 200 in the server 10 examining the operating room information in the received schedule for the schedule medical procedure and determines the first type of dispenser (if more than one first type of dispenser is located in a hospital). Once the first type of dispenser is determined, a processor 200 in the server 10 retrieves the corresponding first type dispenser information 330 from the electronic storage device 205 (e.g., inventory information). When the requested type of medical device is available (and quantity) ("Y" at S50, e.g., available>=requested in electronic preference card), the processor 200 adds the requested type of medical device and amount to the pick list (S52). On the other hand, when the requested type of medical device is not available (quantity) ("N" at S50, e.g., available<requested in electronic preference card), a processor 200 in the server 10 determines whether there is an allowable substitute at S54. A processor 200 in the server 10 looks at the allowable substitutes 320 in the electronic storage device 205 to see if there is a preapproved substitute for the medical product. In an aspect of the disclosure, the electronic preference card 310 may also include data indicating an allowable substitute. If there is an allowable substitute ("Y" at S54), a processor 200 in the server 10 determines if the allowable substitute is available (S50 again).

When the substitute type of medical device is available (and quantity) ("Y" at S50, e.g., available>=quantity of substitute), a processor 200 in the server 10 adds the substitute type of medical device and amount to the pick list (S52). On the other hand, when the substitute type of medical device is not available (quantity) ("N" at S50, e.g., available<quantity of substitute), a processor 200 in the server 10 determines whether there is another allowable substitute at S54. When there is no allowable substitute or another substitute ("N" at S54), a notification may be generated S56. In another aspect of the disclosure, when multiple first type of dispensers are located in a hospital, the server 10 may look to see of another first type of dispenser has the requested type of medical device (and quantity) and issue a pick list to the another first type of dispenser and a corresponding notification indicate that a different dispenser has the type of medical product.

In an aspect of the disclosure, when a substitute type of medical product is included in the pick list or when a pick list does not include all of the types of medical products from an electronic preference card 310 (in the requested quantities), a processor 200 in the server 10 may store in indicator in the electronic storage device 205 in first type disperser data 330 (for the corresponding first type of dispenser). For example, the indication may be a flag. The indication may indicate a partial fill of the electronic preference card data 310. This flag may be used to determine coverage for a Provider-Procedure Pair in order to update the planogram and frequency of ordering inventory as will be described later. The indication may also be transmitted to the first type of dispenser (to cause a light indicator to be displayed on the first type of dispenser). In an aspect of the disclosure, the indication may include the identifier of the substitute medical product and the identifier of the requested medical product to be displayed on the display 416 of the dispenser.

The above process is repeated for each type of medical product in the electronic preference card data (310) and cards for the same medical procedure.

The above process is also repeated for each scheduled medical procedure in the received schedule. The generated pick list(s) are stored in the electronic storage device 205.

At S28, the server 10 transmits the generated pick list(s) to the first type of dispenser. A processor 200 in the server 10 retrieves the generated pick lists from the electronic storage device 205 and schedule and transmits the pick list(s) for one or more schedule medical procedures to the first type of dispenser. The transmission may include a list of identifiers of scheduled medical procedures with its corresponding pick list(s) and time of the scheduled medical procedures (surgery schedule data including the identifier of the medical procedures and time)). In an aspect of the disclosure, the list may be in chronological order by time. In another aspect of the disclosure, the pick list(s) may also include a location identifier of an inventory area 418*a-n* for the each type of medical product. For example, a processor 200 in the server 10, when generating the pick list may look at the planogram for the first type of dispenser and obtain the location identifier for the type of medical product.

In other aspects of the disclosure, the pick list(s) for each scheduled medical procedure may include an instruction to dispense the medical products for the respective scheduled medical procedure to a specific dispensing area 407*a-n*.

In other aspects of the disclosure, the pick list(s) for each scheduled medical procedure may include allowable substitute type of medical products (where available). In this aspect of the disclosure, a processor 200 in the server 10 may retrieve the allowable substitutes 320 associated with the respective medical products in the pick list(s) and where available add them to the pick list(s) with a specific identifier indicating that they are allowable substitutes.

If the first type of dispenser was in a sleep mode, when the first type of dispenser receives the pick lists and schedule, the first type of dispenser wakes up and begins a dispensing processing (job picking mode or dispensing mode). In an aspect of the disclosure, prior to dispensing the medical products, the processor 450 determines whether there is an available dispensing bin (e.g., 405*a*) and the available dispensing bin is located in a dispensing area (e.g., 407*a*) (also referred to as a locker). As described above, the first type of dispenser may comprise a plurality of dispensing bins 405*a-n* and dispensing areas 407*a-n*, one-to-one correspondence.

When the processor 450 determines that there is an available dispensing bin (e.g., 405*a*) and the available dispensing bin is located in a dispensing area (e.g., 407*a*), the processor 450 starts to automatically dispense the medical products for one of the scheduled medical procedures. When multiple pick lists are generated for one medical procedure, the first type of dispenser may combine the medical products picked from the pick lists into one dispensing area (e.g., 407*a*). In other aspects of the disclosure, medical products for different pick lists for the same medical procedure will be dispensed in different dispensing areas. The first type of dispenser may prioritize dispensing based on a time of the scheduled medical procedure. Therefore, the processor 450 may start dispensing according to the pick list(s) for the earliest scheduled medical procedure received. For example, the processor 450 controls the transfer mechanism 430 to move to the appropriate inventory area 418. In an aspect of the disclosure, to determine the location within the dispenser, e.g., inventory area, the processor 450 may use the location identifier corresponding to the medical product from the inventory map (or planogram) which is stored in its electronic storage device. Alternatively, in other aspects of the disclosure, when the location identifiers are included in the pick list, the processor may use the location identifiers in the pick list to determine the inventory area for each medical product to be dispensed. Once at the appropriate area, the transport mechanism reads the identifier of the medical product and moves the medical product to the dispensing bin (e.g., 405*a*). This is repeated for each medical product in the pick list.

After dispensing all of the medical products in a pick list(s) for the scheduled medical procedure, the processor 450 may transmit a confirmation to the server 10. For example, the processor 450 may transmit via the communication interface 475, a confirmation with a time of dispensing to the server 10. In other aspects, the confirmation may wait until all of the scheduled medical procedures (received) is completed. In other aspects, the confirmation may wait until the heartbeat is transmitted to transmit the confirmation.

In an aspect of the disclosure, the confirmation may include a complete list of the medical products (types and quantities of each) that are actually dispensed for the scheduled medical procedure (for each scheduled medical procedure). This list then may be used by the server 10 to update the inventory. In other aspects, the confirmation may only include the types of medical products and quantities where the actual dispensed medical products were different from the types (and quantities) included in the pick list(s).

In another aspect of the disclosure, the dispenser may further transmit an inventory map to the server 10. In an aspect of the disclosure, the inventory map may be included in the confirmation.

The above automated dispensing process is repeated for each available dispensing bin 405*a-n* (and where the same is located in the dispensing area 407*a-n*).

As described above, under certain conditions, such as when an error occurs in the dispensing, the actual medical products may be different from the requested medical products in the electronic preference card 310 and/or the pick list. The error may be, but not limited to, the requested medical product not being available (in the requested quantities), error reading the medical product, such as scanning the wrong location or can't scan, medical product expired, etc. In other aspects of the disclosure, the error also includes a medical product recall. When an error occurs, the processor 450 may try to attempt to automatically dispense the medical type a preset quantity of times, and if continues to fail, the first type of dispenser may use the allowable substitute type of medical product. In an aspect of the disclosure, the first type of dispenser may move the medical product causing the error to an error area 445.

In an aspect of the disclosure, after an error occurs, the processor 450 may report the error to the server 10. The error report may include a quantity of medical products moved to the error area 445. In an aspect of the disclosure, the error report may also include the inventory map.

If there are no available bins 405*a-n* for dispensing, the processor 450 repeats the determination. For example, in an aspect of the disclosure, the processor 450 may repeat the determination a predetermined quantity of times, spaced by a set time. Afterwards, the first type of dispenser may change modes, such as to a sleep mode. The quantity of time and spacing between times may be customized as desired.

At S30, the server 10 receives the confirmation and/or an error report from the dispenser. For example, a processor 200 in the server 10 receives via the communication interface 210 the confirmation and/or error report. This confirmation and/or error report may be stored in the electronic storage device 205 in the first type dispenser information 330.

At S32, a processor 200 in the server 10 updates the inventory in the first type of dispenser in the first type dispenser information 330 (for the corresponding dispenser) using the inventory listed in the confirmation or inventory map (if included) or if the confirmation does not include a list, the information in the pick list. For example, the processor 200 may subtract the quantity of actual dispensed medical products for each type (quantity) from an available quantity for each type of medical product in the list or pick list (which is the actual dispensed medical products when there is no change) to obtain new available quantity. This is performed for each scheduled medical procedure (confirmation received). When a substitute type of medical product was used, the server 10 will note the same in the inventory. A processor 200 in the server 10 may subtract the quantity of the substitute type of medical product dispensed from the available quantity to obtain a new available quantity. In an aspect of the disclosure, a flag may be set. The flag indicates that the pick list is fulfilled, but not yet picked up by a nurse (or medical personnel).

Similarly, at S32, when a processor 200 in the server 10 receives the error report, the processor 200 updates the inventory in the first type of dispenser in the first type dispenser information 330 (for the corresponding dispenser) using the inventory listed in the error report (if any) or the inventory map (if included). For example, a processor 200 in the server 10 may subtract the quantity of medical products (for a type) from an available quantity for each type included in the error report to obtain a new available quantity.

When a nurse (or other medical personnel) retrieves the dispensed medical products from one of the dispensed areas (e.g., 407*a*), the processor 450 transmits a confirmation to the server 10 via its communication interface 475. At S34, the server 10 receives the confirmation and notes the same in the first type dispenser information 330 (for the corresponding dispenser). In an aspect of the disclosure, the flag may be removed to indicate that the medical products were picked up.

In an aspect of the disclosure, the provider can update and/or modify the data of their electronic preference card 310, and/or can request further inventory from the first type of dispenser. For example, when the electronic preference card data 310 is stored in a client device 14 and the client device 14 is in the operating room, the provider can update the request. In this aspect of the disclosure, the update can be sent directly to the first type of dispenser in addition to being sent to the server 10. The dispenser may subsequently dispense the medical products and report the dispensing to the server 10.

As will be described later, a client device may also be able to view screens depicting available inventory in the first type of dispenser. Therefore, when updating the electronic preference card data 310, the provider may be able to confirm the availability of inventory and send the updated electronic preference card 310 to the first type of dispenser (e.g., Kiosk 16) and the server 10. In this aspect of the disclosure, when the first type of dispenser receives the request, since it is aware of the time of the scheduled medical procedure, the updated electronic preference card 310 may be given priority for dispensing. In this aspect, the server 10 may not generate the pick list. The dispensing is performed as described above after it is determined that a dispensing bin (e.g., 405*b*) is available and in a dispensing area (e.g., 407*b*). Once the medical products are dispensed, the processor 450 may generate a confirmation of the picking. This confirmation may include all types of medical products dispensed (and quantities). Upon receipt of this confirmation, in a similar manner as described above, the inventory is updated by the server 10.

At S36, a processor 200 in the server 10 determines whether the server 10 received add-on information from a second type of dispenser (e.g., hub 18 or smart shelves 20). Add-on information means that one or more medical products were removed from a second type of dispenser. For example, before or during a medical procedure, additional medical products may be needed. These additional medical products may be manually obtained from the second type of dispenser.

As described above, the second type of dispenser is able to determine a location of the removal of the medical product (and quantities). In an aspect of the disclosure, the processor 550, 650 may compare the determined location with the location identifier contained in the planogram (and/or inventory map) and transmit the corresponding identifier of the medical product to the server 10 via its communication interface. In other aspects of the disclosure, the processor 550, 650 may transmit the determined location to the server 10 without comparing with the inventory map. In another aspect of the disclosure, when a medical product is removed from a second type of dispenser, hospital personnel may input an operating room number into a display 616 of the second type of dispenser (such as into the display of a smart shelf 20) and the processor 650 transmits the identifier of the medical product or the identifier of the location with the operating room number to the server 10. The operating room number may be used to associate the dispensed medical product with a scheduled medical procedure. In other aspects of the disclosure, when a product is removed a second type of dispenser, hospital personnel may input an identifier of the scheduled medical procedure into a display 616 of the second type of dispenser (such as into the display of a smart shelf 20) and the second type of dispenser transmits the identifier of the medical product or the identifier of the location with the identifier of the scheduled medical procedure to the server 10. In other aspects, both the operating room number and the identifier of the scheduled medical procedure may be input and transmitted to the server 10 when a medical product is dispensed. The information input may be based on the location of the dispenser. For example, if the dispenser is located within an operating room (such as a hub 18, the server 10 already knows the operating room number (and the scheduled medical procedure identifier). However, when the dispenser is external to the operating room in order to associate the dispensed medical products with a scheduled medical procedure, additional information may be necessary.

When a processor 200 in the server 10 receives the identifier of the medical product (or the location identifier) (with or without the above other information), the processor 200 determines that the server 10 received an add-on ("Y" at S36), otherwise, the server 10 continues to wait ("N" at S36). In an aspect of the disclosure, the second type of dispenser also transmits its identifier such that the server 10 knows the dispenser which sent the information.

In an aspect of the disclosure, each time a medical device is removed from the second type of dispenser, the processor 550, 650 transmits the identifier of the medical product (or the location identifier)(with or without the above other information) to the server 10. In other aspects of the disclosure, the processor 550, 650 waits a set time and aggregates the identifiers, and transmits the identifiers in a batch to the server 10 (and quantities for each). The identifiers may be temporarily stored in the electronic storage device 555, 655.

At S38, a processor 200 in the server 10 updates the inventory in the second type dispenser information 335 (for the corresponding dispenser) and associates the dispensed medical product to a scheduled medical procedure. For example, in a case where each time a single medical device is removed from the second type of dispenser, the processor 200 in the server 10 subtracts one (1) from the available quantity for the received identifier of the medical product (type), per time. When the identifier is a location identifier, a processor 200 in the server 10 retrieves the planogram (or inventory map) for the corresponding dispenser to obtain the corresponding identifier of the medical product (type) and then subtracts one (1) from the available quantity. In a case where the second type of dispenser aggregates the identifiers (and quantities for each), a processor 200 in the server 10 subtracts the quantity received for the respective type based on the received identifiers. Similarly, as above, when each identifier is a location identifier, a processor 200 in the server 10 retrieves the planogram (or inventory map) for the corresponding dispenser to obtain the corresponding identifier of the medical products (types). Similarly, a processor 200 in the server 10 adds the quantity for the types of medical products dispensed to dispensed products for the scheduled medical procedure for comparison with the manually entered used medical product information received from the client device 32.

FIG. 11 illustrates a flow chart for a reconciliation process. A nurse or other medical personnel may use a client device 32 to access the server 10. Similar to above, the client device 32 may be a mobile telephone, tablet, portable laptop, personnel computer or any electronic device with a memory and a communication interface. The communication interface may be a wireless communication interface. In other aspects of the disclosure, the communication interface may be a wired communication interface. In some aspects of the disclosure, the client device 32 may have a web browser and access the server 10 via the Internet. In other aspects of the disclosure, the client device 32 may have or download an application program and the application program is configured to access the server 22. In other aspects of the disclosure, the client device 32 may communicate with the server 10 using a file transfer protocol (FTP). In other aspects of the disclosure, the client device 32 may communicate with the server 10 using another secure data transfer method. The client device 32 may be located in the operating room or a nurse's station. The client device 32 may be used to enter used types of medical products (and respective quantities) and unused types of medical products (and respective quantities). The unused types of medical products (and respective quantities) may be subsequently restocked into the first type of dispenser (e.g., kiosk 16) or into a second type of dispenser, e.g., smart shelves 20. To track waste of medical products, the amount of used medical products during a surgery can be added to the amount returned to the restocking inventory (to both), the difference being a waste of medical products. Additionally, the nurse or other medical personnel can manually enter what medical products have been thrown away as waste.

Once transmitted, the server 10 receives the types of medical products (and respective quantities) and unused types of medical products (and respective quantities) from the client device 32. A processor 200 in the server 10 receives the same via the communication interface 210 at S60. The received data may be stored in the electronic storage device 205 in data for the reports 340. This data may also be display on screen in the Platform 350. In an aspect of the disclosure, the received data may be stored in the corresponding dispenser e.g., in the first type dispenser 330 (e.g., Kiosk 16) or second type dispenser 335, such as for the smart shelves 20.

At S62, a processor 200 in the server 10 determines whether there are any medical products to be restocked in the first type of dispenser (e.g., Kiosk 16). For example, the processor 200 determines whether there are unused products which were dispensed from the first type of dispenser. In an aspect of the disclosure, this determination may be made by identifier. In other aspects, this determination may also be made based on whether the server 10 received and add-on information from a second type of dispenser.

In response to determining that there are medical products to be restocked in a first type of dispenser ("Y" at S62), a processor 200 in the server 10 may transmit a notification to the corresponding first type of dispenser at S64. The notification may include the identifier(s) of the medical products to be restocked and quantities of each type. As described above, in other aspects of the disclosure, the notification may include other information such as expiration date and/or product recall. In other aspects, the notification may indicate that products are to be restocked without having the identifier(s) or quantities. In other aspects, the notification may be omitted.

In an aspect of the disclosure, each time a medical product is restocked into an inventory area 418a-n, the processor 450 may transmit a confirmation to the server 10 with the identifier of the medical product. In other aspects of the disclosure, the processor 450 may wait until restocking is completed to transmit the confirmation to the server 10 with all of the identifiers of the medical products (and quantities of each). In yet another aspect of the disclosure, the processor 450 may wait until the heartbeat is transmitted and include the confirmation with all of the identifiers of the medical products (and quantities of each) in the heartbeat. The processor 450 transmits the confirmation via the communication interface 475 to the server 10.

At S66, the server 10 receives the confirmation(s) from the first type of dispenser. A processor 200 in the server 10 stores the information in the electronic storage device 205 in the first type dispenser information 330. In an aspect of the disclosure, the information may also be stored in reports 340.

At S68, the server 10 reconciles the unused medical products entered manually verses the medical products restocked. For each type of medical product, a processor 200 in the server 10 compares the quantity restocked with quantity of unused medical products. When there is a difference, there may have been waste. Additionally, there may be a difference when the dispenser does not hold a medical product that was placed in the restock bin, e.g., might have come from another dispenser. In an aspect of the disclosure, a processor 200 in the server 10 may generate a report 340 or create an indicator and store the same in storage 205 in Platform 350 for subsequent display on a client device, such as in hospital 24 or manufacturer 26. In an aspect of the disclosure, a processor 200 in the server 10 may transmit via the communication interface 210 a notification to a materials manager, such as a push notification. For each type of medical product included in the confirmation, a processor 10 in the server 10 also adds the quantity restocked to an available quantity in the inventory of the first type dispenser information 330 (for the corresponding dispenser).

If at S62, a processor 200 in the server 10 determines that no medical products need to be restocked into a first type of dispenser (e.g., Kiosk 16), the processor 200 determines whether medical products need to be restocked to a second type of dispenser such as the smart shelves 20 (S62A). This determination is similarly based on the identifiers of the unused medical products. In other aspects, the determination may also be based on whether the server 10 receives an add-on from the smart shelves 20. If the processor 200 determines that unused medical products need to be restocked to smart shelves 20, the processor 200 waits until the server 10 receives restock information from the smart shelves 20 until reconciliation.

At S66A, a processor 200 in the server 10 receives the identifiers and/or location identifiers of the medical products restocked from the smart shelves 20, e.g., restock report (and quantities). In an aspect of the disclosure, as described above, the smart shelves 20 may also transmit the reading from the sensor(s) 625. Afterwards, at S68, a processor 200 in the server 10 reconciles the unused medical products entered manually verses the medical products restocked. In an aspect of the disclosure, a processor 200 in the server 10 may wait to reconcile the unused medical products until the server 10 receives a report from a plurality of dispensers. S22-S36 is repeated each time a new schedule is received by the server. S60-S68 is repeated for each scheduled medical procedure.

In an aspect of the disclosure, a processor 200 in the server 10 monitors the expiration dates of the medical products in each dispenser. The first type dispenser information 330 and the second type dispenser information 335 includes the expiration date of the medical products contained in the respective dispensers. The processor 200 may generate a notification for display and store the same in storage 205 in the Platform 350 for subsequent display on a client device (in hospital 24 or manufacturer 26) when a medical product is about to expire. For example, "about to expire" means a preset period of time prior to the expiration date. This preset period of time is customizable and may be set by a hospital administration or materials manager. In an aspect of the disclosure, a push notification may be generated to display on the material managers client device. In an aspect of the disclosure, the notification may be transmitted to the corresponding dispenser for removal, such as display on one of the displays 416. For example, the first type of dispenser after receipt of the notification and when the replenishment mode is started, the first type of dispenser may display the notification on display 416. This will enable a person replenishing the inventory to remove the expired medical products or medical products about to expire.

The notification may include the identifier of the medical products, the location identifiers and quantities.

Figure 12:
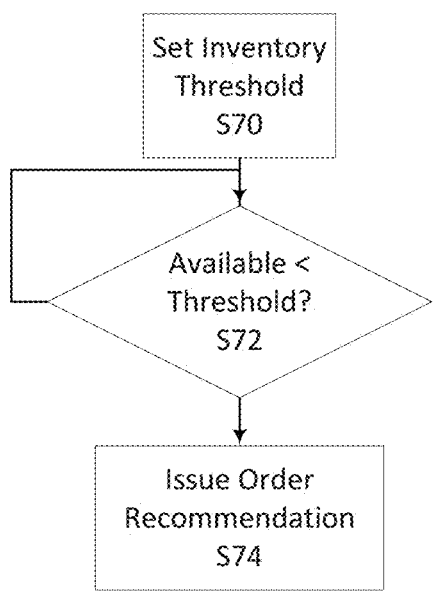

FIG. 12 illustrates a flow chart for inventory management in accordance with aspects of the disclosure. At S70, a processor 200 in the server 10 sets a threshold for the inventory. This threshold may be subsequently used to determine whether to issue a recommendation for purchasing new medical products such as a replenish (or replenishment order). In an aspect of the disclosure, hospital personnel may select the threshold in advance such that the threshold is fixed. In an aspect of the disclosure, the same threshold may be used for each type of medical product. In other aspects of the disclosure, a different threshold may be used for each type of medical product and also be fixed. This initial threshold may be set based on the historical medical procedure information 300 received prior to initial deployment.

In other aspects of the disclosure, this threshold may vary according to usage. For example, a processor 200 in the server 10 may use the trends in the medical product usage to predict future usages using artificial intelligence, such as machine learning (ML) models. Any known machine learning model may be used. For example, a convolutional neural network (CNN) may be used. The trends may include, but are not limited to, seasonality, health patterns, current epidemics and surgery schedule. The trends may also include expiration dates relative to current date. Similar to above, a different threshold may be used for different types of medical products. The threshold may also account for lead time for delivery of the medical product from the manufacturer 26.

Once set, a processor 200 in the server 10 continuously monitors the inventory quantities of each type of medical devices in each dispenser. The processor 200 compares the available inventory (current inventory) with the threshold (current set threshold) for each type of medical product for each dispenser at S72. When the available inventory for a type of medical product is less than its corresponding threshold ("Y" at S72), a processor 200 in the server 10 issues a recommendation for ordering the type of medical product at S74 (such as a replenish order). In an aspect of the disclosure, this recommendation maybe a push notification to a materials manager's screen in a Platform 350. The recommendation may be stored in the electronic storage device 205 in Platform 350. In other aspects of the disclosure, the server 10 may generate an email to the materials manager. In another aspect of the disclosure, the recommendation may be sent to the manufacturer 26. In this aspect of the disclosure, the manufacturer 26 may be able reduce the lead time for transmitting the medical products to a hospital 24.

In an aspect of the disclosure, the recommendation may be for a fixed quantity. The fixed quantity may be different for different types of medical products. This fixed quantity may be set in advance by a hospital administrator or materials manager. In other aspects of the disclosure, this fixed quantity may be determined by a processor 200 in the server 10 prior to initial deployment using the historical medical procedure information 300.

In other aspects of the disclosure, a processor 200 in the server 10 may determine the quantity based on usage. For example, a processor 200 in the server 10 may use the trends in the medical product usage to forecast future usages using artificial intelligence, such as machine learning (ML) models. Any known machine learning model may be used. For example, a convolutional neural network (CNN) may be used. The trends may include, but are not limited to, seasonality, health patterns, current epidemics and surgery schedule. The trends may also include expiration dates relative to current date. Similar to above, different amounts may be used for different types of medical products.

In other aspects of the disclosure, the recommendation may not include a quantity. Further in other aspects of the disclosure, in addition to a push notification being sent to the materials manager (or hospital administrator), the recommendation may be viewable on a screen(s) by nurses and other hospital personnel, hospital 24 and/or the manufacturer 26. In other aspects, the recommendation may also be transmitted from the server 10 to the specific dispenser.

In an aspect of the disclosure, medical products may be ordered using the platform 350. For example, when the recommendation is displayed on screen(s) in the platform 350, the recommendation may be in a form of a link to clink on to order the recommended amount. When the link is clicked on, and the order is confirmed, a purchase order may be sent to the manufacturer 26.

In other aspects of the disclosure, instead of or in addition to the recommendation, a processor 200 in the server 10 may issue a purchase order (PO) to the manufacturer 26 for the type of medical product. The PO may be for a preset quantity. In response to the PO being received by the manufacturer 26, the manufacturer 26 forwards the same to a distribution center 28 near the hospital 26 for product shipping 30 to the hospital 26.

To effect movement of the medical products located at the distribution center 28, the medical products can be shipped from the distribution center 28 to the hospital 24 by any suitable shipment apparatus, such as by truck, train, airplane, drone, car, boat, etc. Upon arrival of medical products to the hospital 24, the boxes of medical products can brought to the appropriate dispensers for replenishing as described above.

While FIG. 12 shows one threshold for each type of medical products, multiple thresholds may be used. For example, a first threshold may be used to issue a first recommendation for a quantity and a second threshold may be used to issue a second recommendation for a larger quantity (where the second threshold is less than the first threshold). The different recommendations may be displayed in a different manner. For example, the first recommendation may be displaced in a first color and the second recommendation may be displayed in a second color. In other aspects, the first threshold may be used to issue a recommendation for a quantity and the second threshold may be used to issue a PO for a preset quantity (where the second threshold is less than the first threshold).

In an aspect of the disclosure, a processor 200 in the server 10 may analyze the data from the reconciliation for a scheduled medical procedure and/or electronic provider preference card 310 and either generate a report 340 or make the analysis available on a screen(s) for display on a client device such as at a hospital 24 or manufacturer. For example, a processor 200 at the server 10 may for each type of medical product, calculate a percentage of used medical product to requested medical product from the electronic provider preference card 310. Additionally, a percentage may be calculated in aggregate for all of the used medical products to all requested medical products from the electronic provider preference card. Similar calculation may be made for the unused medical products.

Additionally, a processor 200 in the server 10 may calculate a percentage of add-on medical products per type verses the requested medical products from the electronic provider preference card 310.

The results of the calculations may be stored in reports 340 in the electronic storage device 205 for display. For example, hospital personnel may view the analysis on the screen(s) and make recommendations for updating a provider electronic preference card 310.

In an aspect of the disclosure, a processor 200 in the server 10 may analyze the used and unused medical product information and/or add-on information for a specific provider across multiple procedures. For example, since the schedule may contain an identifier of the provider, a processor 200 in the server 10 may analyze the used and unused medical product information from the reconciliation from all medical procedures for the specific provider. The analysis may include calculating percentages per type of medical product and/or aggregating all types of medical products. The analysis may be for used, unused, and/or add-on information for the specific provider.

This analysis may be stored in the electronic storage device 205 in reports 340. In an aspect of the disclosure, the analysis may be displayed on screen(s) in the Platform 350. Hospital personnel may view the analysis on the screen(s) and make recommendations for updating the provider electronic preference cards 310 for the specific provider.

In some aspects, a processor 200 in the server 10 may recommend changes in the electronic preference card 310 for the specific provider. For example, the recommendation may include alternative identifiers of medical products that have similar characteristics to the products that the provider is using and are clinically acceptable. In other aspects, the recommend may be to reduce or add quantities for a medical product for an electronic preference card 310. For example, if a provider consistently lists a larger quantity for a medical product than used in medical procedures, the recommendation may be to reduce the requested quantity (and vice versa).

In an aspect of the disclosure, a processor 200 in the server 10 may analyze the used and unused medical product information and/or add-on information for a specific medical procedure across multiple electronic provider cards 310 from different providers. For example, since the schedule may contain an identifier of the scheduled medical procedure(s), a processor 200 in the server 10 may analyze the used and unused medical production information from the reconciliation from all electronic provider cards 310 for the type of the medical procedure (e.g., knee surgeries). The analysis may include calculating percentages per type of medical product and/or aggregating all types of medical products. The analysis may be for used, unused, and/or add-on information for the specific type of medical procedure. This analysis may be stored in the electronic storage device 205 in reports 340. In an aspect of the disclosure, the analysis may be displayed on a screen(s) of the Platform 350. Hospital personnel may view the analysis on the screen(s) of the Platform 350 and make recommendations for updating the provider electronic preference cards 310 for the specific type of medical procedure.

In some aspects, a processor 200 in the server 10 may recommend changes in the electronic preference card 310 for the specific type of medical procedure. For example, the recommendation may include alternative identifiers of medical products that have similar characteristics to the products that the provider is using and are clinically acceptable. In other aspects, the recommend may be to reduce or add quantities for a medical product for an electronic preference card 310 for a specific medical procedure. For example, the recommendation may indicate that providers are not using a specific type of medical product or the providers are consistently requesting too many of a specific type of medical product. For example, the recommend may include the number of cases in a time where the specific type of medical product or quantities were not used and a recommend number or recommendation to remove the specific type of medical product.

In addition to the above analysis, the manufacturer 26 and/or hospital 24 may access the data in the electronic storage device 205 for viewing on a screen(s) of the Platform 350 via client terminals including but not limited to the first type dispenser information 330, second type dispenser information 335, reports 340, recall notices 325, allowable substitute 320, scheduled medical procedures 315 and electronic preference card data 310.

Similar to above, the client device may be a mobile telephone, tablet, portable laptop, personnel computer or any electronic device with a memory and a communication interface. The communication interface may be a wireless communication interface. In other aspects of the disclosure, the communication interface may be a wired communication interface. In some aspects of the disclosure, the client device may have a web browser and access the server via the Internet. In other aspects of the disclosure, the client device may have or download an application program and the application program is configured to access the server.

The specific information available for viewing is limited by access rights. When a person logins into the server 10, they may use a user name and passcode. A processor 200 in the server 10 authenticates the person using the stored credentials 345. Once authenticated, the processor 200 transmits screens containing data from the storage device 205 based on the access rights. A template for the screens is stored in Platform 350. The templates for the screens may differ depending on the type of client device accessing the server. For example, the templates may be different for a mobile phone, tablet and a laptop/desktop.

In other aspects of the disclosure, the server 10 may communicate with the manufacturer 26 outside of the platform. For example, the server 10 may communicate via FTP. In some aspects, the server 10 may send medical product usage data to the manufacturer 26. In other aspects of the disclosure, the server 10 may send inventory data in each dispenser to the manufacturer 26. In other aspects of the disclosure, the server 10 may send forecasts for medical products to the manufacturer 26. This information may be used for manufacturing planning. For example, the manufacturer 26 can use any or all of this data to estimate future medical product manufacturing needs for individual hospitals 24, and can estimate manufacturing and shipping times for the future medical products.

In an aspect of the disclosure, the server 10 may determine a forecast for medical products for a period of time using the information of scheduled medical procedures 310, electronic card preference data 310, inventory in the dispensers (first type dispenser information 330 and second type dispenser information 335). The forecast may be for a longer period of time than the when determine when and how many medical products to order as described above. In some aspects of the disclosure, the determination may be based on machine learning. Any known machine learning model may be used. For example, a convolutional neural network (CNN) may be used.

Figure 13:
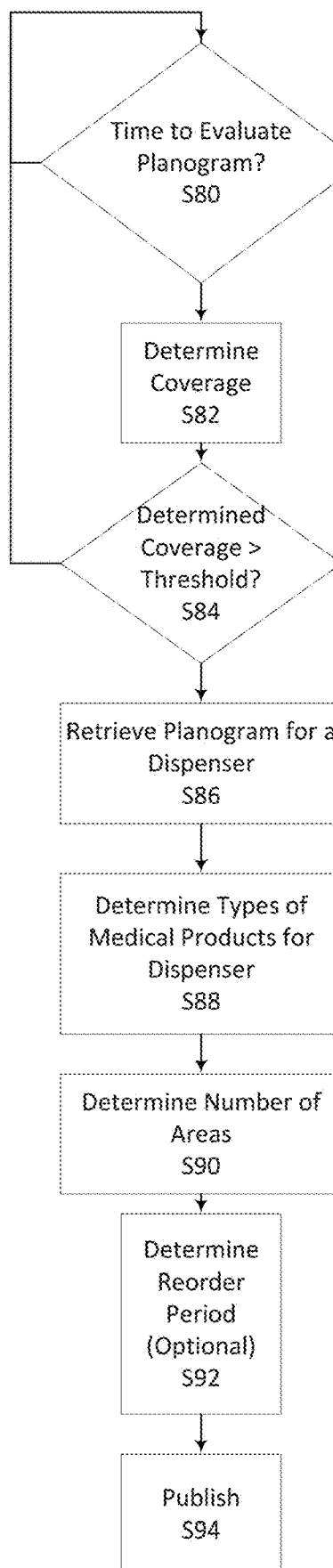

FIG. 13 illustrates a flow chart for updating a planogram in accordance with aspects of the disclosure. At S80, a processor 200 in the server 10 determines whether it is time to determine whether to update a planogram for a dispenser, e.g., evaluation time. This is done for each dispenser in the system. The timing for the evaluation may preset. For example, the timing may be daily, weekly, monthly, quarterly, etc. In an aspect of the disclosure, the time may be determined by a hospital administrator or other hospital personnel such as a materials manager. In other aspects, the manufacturer 26 may determine the timing. In other aspects of the disclosure, the timing may be an on-demand request from hospital administrator or other hospital personnel such as a materials manager. For example, a hospital administrator or other hospital personnel such as a materials manager may issue a request to evaluate the planogram when inventory is ordered for a specific type of medical products more frequently than desired.

When the current time is equal to the timing or in response to the on-demand request ("Y" at S90), a processor 200 in the server 10 determines the coverage for the dispenser (S92). In other aspects of the disclosure, a counter/timer may be set to a time (e.g., weekly, monthly, quarterly) and when the counter expires, it is determined that it is time to evaluate the planogram.

The coverage is determined based on a percentage of complete fillings (picking) of all types and quantities of the electronic provider preference cards 310 for Provider-Procedure Pairs during the period to total electronic provider preference card 310 for all Provider-Procedure Pairs. A complete filling (picking) is one where there is no partial filling flag as described above. In some aspects, the complete filling may also include picking lists where substitute type medical products were also included in the pick list. In other aspect, when a substitute type medical product is used, the pick list is not included in the complete fillings.

A processor 200 in the server 10 calculates the coverage percentage and then compares the calculated coverage percentage with a threshold at S84. When the determined coverage is higher than the threshold ("Y" at S84) there is no need to update the planogram. On the other hand, when the determined coverage is lower than the threshold ("N" at S84), the planogram and/or frequency in ordering inventory needs to be updated.

At S86, a processor 200 in the server 10 obtains a planogram for the specific dispenser that it is evaluating from the electronic storage device 205 (in planograms 305).

At S88 and S90, a processor 200 in the server 10 determines the types of medical devices and quantity of areas for each medical device to be included in the respective dispenser. In an aspect of the disclosure, this may be determined using dispenser medical procedure information for the type of dispenser (either first type dispenser information or second type dispenser information) for the corresponding dispenser for the previous period. In an aspect of the disclosure, the determination may also include information from more than one previous period for the dispenser and/or information from other dispensers and/or the historical medical procedure information. In some aspects, the processor may only use the medical procedure information relevant to the location of the dispenser. For example, if the dispenser is a first type dispenser and will be located near a specific core, the processor 200 may only use the medical procedure information for the operating rooms in the core. In an aspect of the disclosure, the processor 200 may used the dispenser medical procedure information for all previous periods, and not just one period.

In an aspect of the disclosure, a processor 200 in the server 10 may use similar methods as described above for the determinations. In other aspects, as shown in FIG. 13, the server 10 may also determine the target inventory reorder period at S92 in a similar manner as described above.

Once the planogram is repopulated with the identifiers of the medical products for each inventory area, a processor 200 in the server 10 publishes the planogram 305 in the electronic storage device 205.

S80-S94 are repeated for each first type of dispenser.

While FIG. 1 shows a hospital 24, the server 10 may managing inventory and dispensers in different hospitals and generate forecast for medical products from multiple different hospital.

As used herein, the term "processor" may include a single core processor, a multi-core processor, multiple processors located in a single device, or multiple processors in wired or wireless communication with each other and distributed over a network of devices, the Internet, or the cloud. Accordingly, as used herein, functions, features or instructions performed or configured to be performed by a "processor", may include the performance of the functions, features or instructions by a single core processor, may include performance of the functions, features or instructions collectively or collaboratively by multiple cores of a multi-core processor, or may include performance of the functions, features or instructions collectively or collaboratively by multiple processors, where each processor or core is not required to perform every function, feature or instruction individually.

The phrase "communication interface" includes electronic circuitry, configured for one more specific standards, that enables one device to telecommunicate (transmit and receive) with another device.

The various aspects disclosed herein can be implemented in various forms of hardware, software, firmware, and/or special purpose processors. For example, in an aspect of the disclosure, at least one non-transitory computer readable storage medium has instructions encoded thereon that, when executed by one or more processors, cause one or more of the aspects disclosed herein to be implemented. The instructions can be encoded using a suitable programming language, such as C, C++, object oriented C, Java, JavaScript, Visual Basic .NET, Beginner's All-Purpose Symbolic Instruction Code (BASIC), or alternatively, using custom or proprietary instruction sets. The instructions can be provided in the form of one or more computer software applications and/or applets that are tangibly embodied on an electronic storage device, and that can be executed by a computer having any suitable architecture. The computer software applications disclosed herein may include any number of different modules, sub-modules, or other components of distinct functionality, and can provide information to, or receive information from, still other components.

Numerous specific details have been set forth herein to provide a thorough understanding of the disclosure. It will be understood by an ordinarily-skilled artisan, however, that the aspects of the disclosure may be practiced without these specific details. In other instances, well known operations, components and circuits have not been described in detail so as not to obscure the disclosure. It can be appreciated that the specific structural and functional details disclosed herein may be representative and do not necessarily limit the scope of the aspects of the disclosure. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, and aspects have been described herein. The feature and aspects are susceptible to combination with one another as well as to variation and modification, as will be understood by those having skill in the art. The present disclosure should, therefore, be considered to encompass such combinations, variations, and modifications. It is intended that the scope of the present disclosure not be limited by this detailed description, but rather by the claims appended hereto. Future filed applications claiming priority to this application may claim the disclosed subject matter in a different manner, and may generally include any set of one or more elements as variously disclosed or otherwise demonstrated herein.

While the present disclosure has been particularly shown and described with respect to preferred aspects thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A system comprising:
an interface accessible from a plurality of client devices, the interface enabling one or more requests for types of medical products and a quantity for each type to be sent to a server for an identified medical procedure;

a dispenser comprising:
  a plurality of inventory areas for types of medical products, where a type of medical product is storable in a respective area of the plurality of inventory areas;
  a plurality of dispensing bins to receive and store dispensed medical products for scheduled medical procedures, respectively;
  one or more readers configured to read an identifier on medical products or a box of medical products,
  a first electronic storage device;
  a first communication interface, and
  a first processor,
the server comprising:
  a second communication interface;
  a second electronic storage device configured to store a database, the database comprising information on scheduled medical procedures, the information on scheduled medical procedures including requested types of medical products and quantity for each for the identified medical procedure and an identifier of a person who requested the types of medical products, an identifier of the respective scheduled medical procedure, the database further comprising an inventory for each type of medical products, the inventory including, for each type of medical product in the dispenser, the identifier of the medical product, an available quantity of the medical product and an expiration date;
  a second processor configured to:
    receive the one or more requests from one or more client devices;
    update the database based on the one or more requests;
    when a schedule for one or more scheduled medical procedures for a period of time is confirmed, the second processor is configured to cause the second communication interface to transmit to the dispenser the schedule having one or more pick lists for each of the one or more scheduled medical procedures for the period of time, the one or more pick lists for each of the one or more scheduled medical procedures for the period of time includes the identifier of the scheduled medical procedure and an identifier of each type of medical product and quantity of each to be dispensed, the schedule indicating a time of each of the one or more scheduled medical procedures,
wherein in response to receipt of the schedule with the one or more pick lists for each of the one or more scheduled medical procedures for the period of time, the first processor is configured to determine whether at least one of the plurality of dispensing bins for storing dispensed medical products is available and located in one of a plurality of dispensing areas, and in response to determining that at least one of the plurality of dispensing bins is available and located in one of the plurality of dispensing areas, the first processor is configured to cause, for an available bin, an automatic dispensing of the medical products for a pick list of the one or more pick lists for each of the one or more scheduled medical procedures included in the received schedule, the automatic dispensing comprises retrieving the medical products from the corresponding inventory areas and placing the medical products in the one of the plurality of dispensing bins in the dispensing area for the pick list.

2. The system of claim 1, wherein the schedule with the one or more pick lists for each of the one or more scheduled medical procedures for the period of time further includes location identifiers indicating a location of the inventory areas of the types of medical products, respectively from among the plurality of inventory areas, to be dispensed for each of the one or more pick lists for each of the one or more scheduled medical procedures, and the first processor is configured to cause the retrieval of the medical products using the location identifiers indicating the location.

3. The system of claim 1, wherein in response to determining that at least one of the plurality of dispensing bins is not available, the first processor is configured to repeat the determination.

4. The system of claim 1, wherein when the dispensing based on the received schedule is complete or when the dispensing of one pick list is complete, the first processor is configured to cause the dispenser to transmit, via the first communication interface, a confirmation to the server, the confirmation including the types of medical products and quantities dispensed for each pick list that is completed, and
  wherein in response to receipt of the confirmation, the second processor is configured to update the database.

5. The system of claim 1, wherein the one of the one or more readers is configured to scan one or more boxes of medical products for replenishing medical products,
  wherein the first processor is configured to transmit, via the first communication interface, a confirmation after changing a mode of operation, the confirmation including one or more identifiers of the one or more boxes, and
  wherein in response to receipt of the confirmation, the second processor is configured to update the database.

6. The system of claim 1, wherein the dispenser further comprises a restocking area configured to store medical products which were previously dispensed and unused in a scheduled procedure,
  wherein the first processor is configured to cause the dispenser to determine whether the restocking area contains medical products for restocking and in response to the determination, the first processor is configured to cause the dispenser to restock the medical products from the restocking area when the type of medical product is a type of medical product stored in the dispenser.

7. The system of claim 6, wherein the restocking comprises for each medical product:
  scanning the identifier of the medical product with an internal reader;
  determining the corresponding inventory area of the plurality of inventory areas for the type; and
  placing the medical product in the corresponding inventory area.

8. The system of claim 6, wherein upon completion of restocking or periodically, the first processor is configured to cause the dispenser to transmit, via the first communication interface, a confirmation to the server for reconciliation, the confirmation including the type of medical product and quantity of each type.

9. The system of claim 6, wherein dispensing medical products to the plurality of dispensing bins has priority over restocking.

10. The system of claim 9, wherein in response to receipt of a new schedule having one or more pick lists for a scheduled medical procedure and determining that one of the plurality of dispensing bins is available and located in one of the plurality of dispensing area or a pick list contained in a previous schedule had not been completed and determining that one of the plurality of dispensing bins is available and located in one of the plurality of dispensing area, the first processor is configured to cause the dispenser to interrupt the restocking, the interrupt being after a completion of restocking any scanned medical products at the time of receipt of the new schedule or determination.

11. The system of claim 6, wherein the server is configured to receive the quantity of used and unused medical products in a medical procedure from a client device, for each type of medical device in the one or more pick lists for the medical procedure, and
wherein the second processor is configured to compare the quantity of unused medical products for each type of medical devices, with the quantity of restocked medical products for each type of medical devices received from the dispenser for reconciliation.

12. The system of claim 11, wherein in response to a discrepancy in the quantity of unused medical products and the quantity of restocked medical products, the second processor is configured to cause the server to transmit, via the second communication interface, a notification to materials management or update a screen on a web-based user portal.

13. The system of claim 1, wherein the dispenser further comprises an error bin, and wherein the dispenser in dispensing medical products to the dispensing bins is configured to scan a medical product using an internal reader, upon determining a medical product has expired, the first processor is configured to cause the dispenser to place the expired medical product in the error bin.

14. The system of claim 1, wherein the received schedule further includes for at least one type of medical product, an allowable substitute medical product, wherein in response to an error in attempting to dispense the at least one type of medical product, the first processor is configured to cause the dispenser to dispense the allowable substitute medical product for the scheduled medical procedure in the schedule with the pick list and place the allowable substitute medical product in the appropriate dispensing bin.

15. The system of claim 14, wherein the error comprises attempting to retrieve the at least one type of medical product a set quantity of times.

16. The system of claim 14, wherein the dispenser further comprising a light indicator, and wherein when the allowable substitute medical product is dispensed in the dispensing bin, the light indicator is configured to emit a set color different than when the dispensing bin in the dispensing area does not include the allowable substitute medical product.

17. The system of claim 14, wherein when the allowable substitute medical product is dispensed, the dispenser is configured to transmit to the server a confirmation indicating the type of medical products dispensed and the quantity, the type including the allowable substitute medical product.

18. The system of claim 1, further comprising:
a second type of dispenser containing a plurality of types of medical products, the second type of dispenser having a third communication interface which is configured to communicate with the server, wherein when a medical product is removed from the second type of dispenser, the second type of dispenser is configured to identify the type of medical product and transmit the type of medical product that was removed to the server; and
wherein the second processor is configured to update the database based on the received type of medical products from the second type of dispenser.

19. The system of claim 1, wherein the second processor is configured to generate a message when a quantity of available medical product for a type is less than a threshold, the quantity of available medical product determined based on the updated database including information from the dispenser.

20. The system of claim 11, wherein the second processor is configured to analyze, for each type of medical product, the used and unused medical products, for the same medical procedure over a time, using the information in the database and generate a report containing the analysis, the analysis including a recommended type and quantity for each recommended type for the same medical procedure.

21. The system of claim 11, wherein the second processor is configured to analyze, for each type of medical product, the used and unused medical products, for the same provider over a time, using the information in the database and generate a report containing the analysis, the analysis including a recommended type and quantity for each recommended type of medical product.

22. The system of claim 20, wherein the reports are accessible via Internet.

23. The system of claim 20, wherein the second processor is configured to analyze for each type of medical product, the used and unused medical products, for medical procedures over a time, and based on the analysis issue a recommendation for ordering new medical products.

24. The system of claim 1, wherein the medical products are selected from a group consisting of sutures, clips, fasteners, implants, hemostats (absorbable), orthopedic pins, screws, rods, plates, staple reloads, dressings, pacing wires, an endoscope, a clamp, a saw, bone wax, drains, connectors, adapters, tubing, and topical skin adhesives.

25. The system of claim 1, wherein the plurality of inventory areas comprises storage cartridges.

26. The system of claim 1, wherein the interface is accessible via Internet.

27. The system of claim 1, further comprising a third processor configured to: determine the types of medical products to be stored in the plurality of inventory areas; and for the determined type, determine a quantity of the plurality of inventory areas assigned, wherein the determinations are sent to the second processor.

28. The system of claim 27, wherein the determinations are based on historical medical product use information received from a hospital where the dispenser is to be deployed for a plurality of medical procedures for a period of time, the third processor is configured to output a first coverage based on the determinations.

29. The system of claim 28, wherein a coverage is periodically determined based on the updated database and when the determined coverage is a threshold less than the first coverage, the third processor executes the determination of the types of medical products to be stored in the plurality of inventory areas; and for the determined type, and the determination of the quantity of the plurality of inventory areas assigned again.

30. The system of claim 1, wherein the server is further configured to transmit via the second communication interface, inventory data from the database to one or more client devices for display on a screen.

31. The system of claim 30, wherein the inventory data transmitted is based on access rights for users of the one or more client devices.

32. The system of claim 1, wherein all pick lists of the one or more pick lists for the same medical procedure are dispensed in the same available dispensing area.

33. The system of claim 1, wherein, the first processor, for each available bin, causes an automatic dispensing of the medical products for a respective pick list of the one or more pick lists for each of the one or more scheduled medical procedures included in the received schedule, the automatic dispensing comprises retrieving the medical products from the corresponding inventory areas and placing the medical products in a respective one of the plurality of dispensing bins in a respective one of the plurality of dispensing areas.

34. A system comprising:
- an interface accessible from a plurality of client devices, the interface enabling one or more requests for types of medical products and a quantity for each type to be sent to a dispenser for an identified medical procedure;
- a dispenser comprising:
  - a plurality of inventory areas for types of medical products, where a type of medical product is storable in a respective area of the plurality of inventory areas;
  - a plurality of dispensing bins to receive and store dispensed medical products for scheduled medical procedures, respectively;
  - one or more readers configured to read an identifier on medical products or a box of medical products,
  - a first electronic storage device;
  - a first communication interface, and
  - a first processor configured to receive the one or more requests for types of medical products and the quantities for each type via the first communication interface; and cause the dispenser to automatically dispense the requested types of medical products and the requested quantities for each type when available, to a dispensing bin, when the dispensing bin is available and in a dispensing area.

35. The system of claim 34, further comprising:
the server comprising:
- a second communication interface;
- a storage device configured to store a database;
- a second processor, wherein after the dispenser automatically dispensing the requested types of medical products and the requested quantities for each type, the second processor receives confirmation from the dispenser via the second communication interface and updates the database based on the confirmation.

* * * * *